US012594419B2

(12) United States Patent
Teague et al.

(10) Patent No.: US 12,594,419 B2
(45) Date of Patent: Apr. 7, 2026

(54) IMPLANTABLE MEDICAL DEVICE LEAD WITH MODULAR ELECTRODE

(71) Applicant: Pacesetter, Inc., Sylmar, CA (US)

(72) Inventors: Bryan Teague, Canyon Country, CA (US); Kyle Nix, Arcadia, CA (US); Xiangqun Chen, Santa Clarita, CA (US); Joseph Lane Hansen, Los Angeles, CA (US)

(73) Assignee: Pacesetter, Inc., Sylmar (CA)

( * ) Notice: Subject to any disclaimer, the term of this patent is extended or adjusted under 35 U.S.C. 154(b) by 342 days.

(21) Appl. No.: 18/312,478

(22) Filed: May 4, 2023

(65) Prior Publication Data

US 2023/0381496 A1       Nov. 30, 2023

Related U.S. Application Data

(63) Continuation-in-part of application No. 17/804,041, filed on May 25, 2022, now Pat. No. 12,377,262.

(51) Int. Cl.
*A61N 1/05*          (2006.01)
*A61N 1/39*          (2006.01)

(52) U.S. Cl.
CPC ......... *A61N 1/0504* (2013.01); *A61N 1/3956* (2013.01)

(58) Field of Classification Search
None
See application file for complete search history.

(56) References Cited

U.S. PATENT DOCUMENTS

| | | | |
|---|---|---|---|
| 7,363,083 B2 | 4/2008 | Bardy et al. | |
| 8,483,841 B2 | 7/2013 | Sanghera et al. | |
| 9,079,035 B2 | 7/2015 | Sanghera et al. | |
| 10,137,295 B2 | 11/2018 | Marshall et al. | |
| 10,391,325 B2 | 8/2019 | De Kock et al. | |
| 10,661,073 B2 | 5/2020 | Marshall et al. | |
| 2011/0029053 A1* | 2/2011 | North .................. | A61N 1/05 |
| | | | 607/116 |
| 2014/0277311 A1* | 9/2014 | Victorine ............ | A61N 1/05 |
| | | | 607/116 |
| 2016/0021392 A1 | 1/2016 | Bossen et al. | |

(Continued)

FOREIGN PATENT DOCUMENTS

| | | |
|---|---|---|
| EP | 3976167 A1 | 4/2022 |
| WO | 2020243534 A1 | 12/2020 |
| WO | 2022009100 A2 | 1/2022 |

OTHER PUBLICATIONS

User's manual, Emblemtm S-ICD, Electrode Delivery System, Model 4712. © 2017 Boston Scientific Corporation, <https://www. s-icd.es/content/dam/Manuals/US/current-rev-en/360244-001_ EMBLEM_UM_en-USA_S.pdf>, (44 pages).

(Continued)

*Primary Examiner* — Mallika D Fairchild
(74) *Attorney, Agent, or Firm* — Dean D. Small; Carroll, Hoette & Butscher, LLC

(57)          ABSTRACT

A lead for an implantable medical device (IMD) includes an electrode having a plurality of brick segments that are discrete and mechanically connected to one another in a line. The brick segments are electrically conductive and electrically connected to one another. The brick segments are configured to be powered by a pulse generator of the IMD to deliver high-voltage shocks for defibrillation therapy.

20 Claims, 15 Drawing Sheets

(56)　　　　　References Cited

U.S. PATENT DOCUMENTS

| | | | |
|---|---|---|---|
| 2016/0121106 A1* | 5/2016 | Marshall | A61N 1/0504 |
| | | | 607/119 |
| 2020/0376265 A1 | 12/2020 | Sanghera et al. | |
| 2020/0398044 A1 | 12/2020 | Sanghera et al. | |
| 2021/0370080 A1 | 12/2021 | Sanghera et al. | |
| 2021/0370081 A1 | 12/2021 | Sanghera et al. | |

OTHER PUBLICATIONS

Frankel et al., "Impact of Body Mass Index on Safety and Efficacy of the Subcutaneous Implantable Cardioverter-Defibrillator", ACC: Clinical Electrophysiology 2018, vol. 4, No. 5: 652-659, (8 pages).

Quast et al., "A novel tool to evaluate the implant position and predict defibrillation success of the subcutaneous Implantable cardioverter-defibrillator: The PRAETORIAN score", Heart Rhythm 2019, 16: 403-410, (8 pages).

Amin et al, "Factors associated with high-voltage impedance and subcutaneous implantable defibrillator ventricular fibrillation conversion success", Circ Arrhythm Electrophysiol 2019, (10 pages).

Heist et al, "Determinants of subcutaneous implantable cardioverter-defibrillator efficacy: a computer modeling study", JACC Clin Electrophysiol 2017, 3:405-414, (10 pages).

* cited by examiner

500

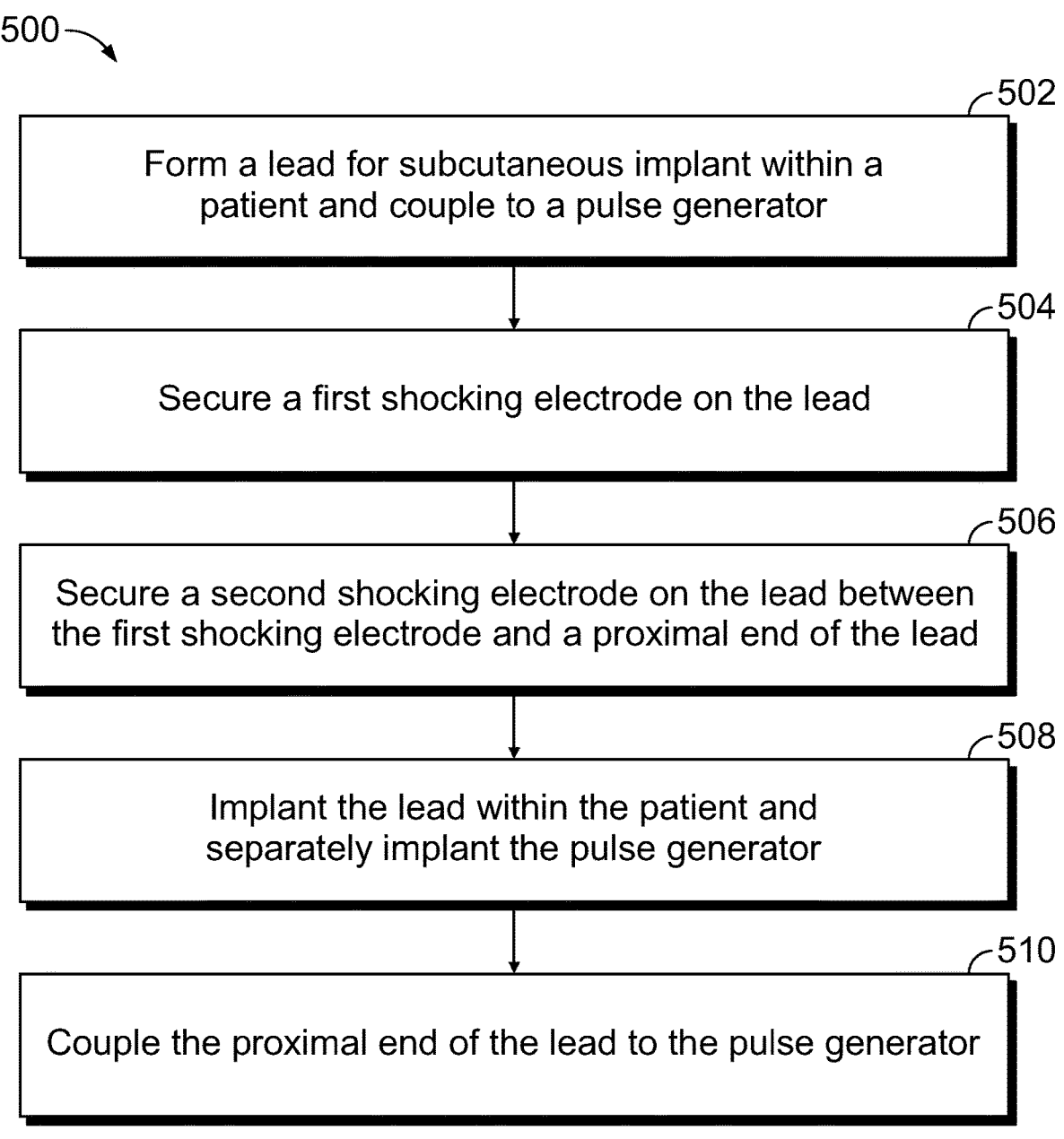

502

Form a lead for subcutaneous implant within a
patient and couple to a pulse generator

504

Secure a first shocking electrode on the lead

506

Secure a second shocking electrode on the lead between
the first shocking electrode and a proximal end of the lead

508

Implant the lead within the patient and
separately implant the pulse generator

510

Couple the proximal end of the lead to the pulse generator

FIG. 5

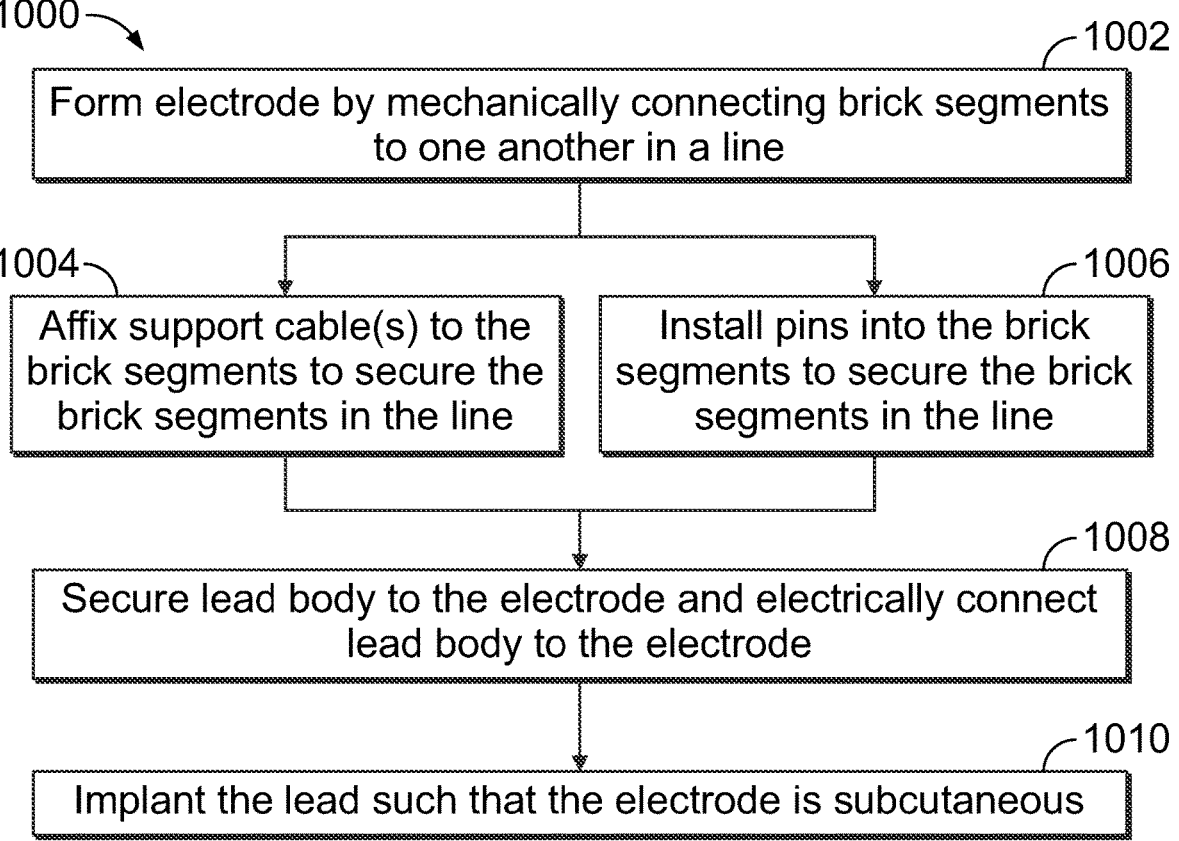

1000

1002

Form electrode by mechanically connecting brick segments to one another in a line

1004

Affix support cable(s) to the brick segments to secure the brick segments in the line

1006

Install pins into the brick segments to secure the brick segments in the line

1008

Secure lead body to the electrode and electrically connect lead body to the electrode

1010

Implant the lead such that the electrode is subcutaneous

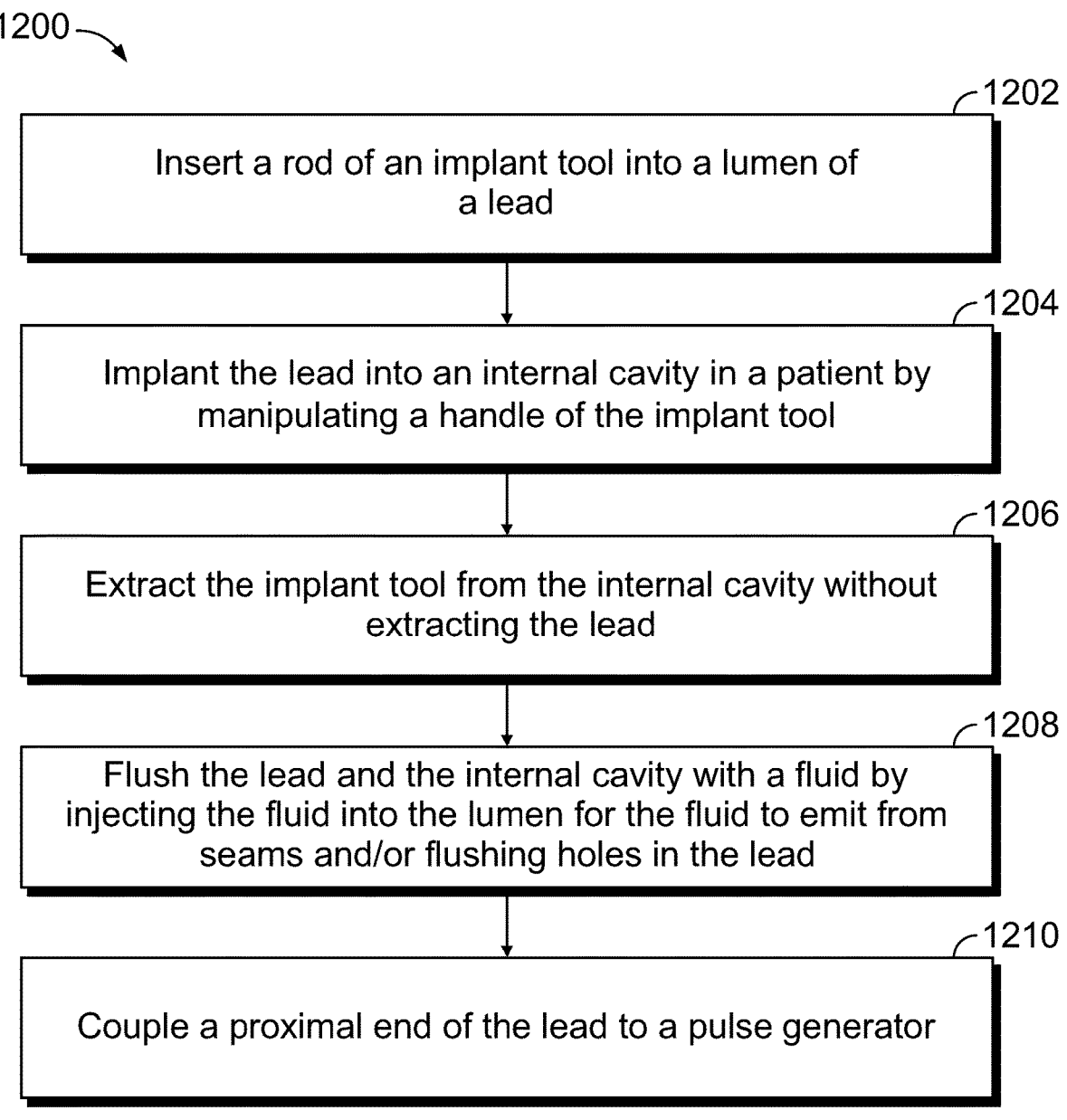

1202

Insert a rod of an implant tool into a lumen of a lead

1204

Implant the lead into an internal cavity in a patient by manipulating a handle of the implant tool

1206

Extract the implant tool from the internal cavity without extracting the lead

1208

Flush the lead and the internal cavity with a fluid by injecting the fluid into the lumen for the fluid to emit from seams and/or flushing holes in the lead

1210

Couple a proximal end of the lead to a pulse generator

FIG. 18

IMPLANTABLE MEDICAL DEVICE LEAD WITH MODULAR ELECTRODE

CROSS-REFERENCE TO RELATED APPLICATIONS

This application is a continuation-in-part application of, and claims priority to, U.S. patent application Ser. No. 17/804,041, titled Method And Implantable Medical Device For Reducing Defibrillation Impedance, which was filed on 25 May 2022, the complete subject matter of which is expressly incorporated herein by reference in its entirety.

FIELD

Embodiments of the present disclosure generally relate to leads of implantable medical devices (IMDs) designed to deliver defibrillation therapy. In one or more embodiments, the leads have at least one modular electrode formed of a line of multiple discrete interconnected components. In one or more embodiments, the modular electrodes may have low impedance for the defibrillation therapy. In one or more embodiments, the leads may be designed for subcutaneous placement within a patient.

BACKGROUND

Some IMDs include circuitry that monitors a patient's heart rhythm to detect arrythmias, such as ventricular tachycardia and/or atrial fibrillation. In response to detecting an arrythmia, the same or a different IMD may deliver a powerful electrical shock to defibrillate the heart. For example, implantable cardioverter defibrillators (ICDs) are IMDs which include a battery-operated generator that generates high voltage shocks and at least one lead extending from the generator to deliver the shocks. Some ICD leads are intra-cardiac and/or transvenous, such that the leads are introduced on or in heart tissue or in surrounding blood vessels.

Some ICD systems are subcutaneous and deliver defibrillation therapy without any intra-cardiac or transvenous leads. The subcutaneous ICDs (S-ICD) include at least one subcutaneous lead extending from the generator. The subcutaneous lead is implanted below the skin but outside of the cardiac tissue and blood vessels. The subcutaneous lead may be implanted along an exterior of the rib cage. The lead may be proximate to the sternum. S-ICD systems eliminate risks associated with transvenous and/or intra-cardiac implanted leads, such as infections and lead failures that may require surgical intervention.

A drawback of known S-ICD systems is the relatively large size of the generator device. The size may be attributable, at least in part, to the power circuitry used to power the defibrillation therapy. For example, to provide shocks to the heart through intervening biologic tissues with sufficient energy to achieve cardioversion (e.g., restoration of normal heart rhythm), the generator may include a significant volume of energy storage onboard, such as multiple capacitors, to power the shocks. For example, the generator may be controlled to convey electrical power on the order of 1200 V or more to the lead for the shocks. The large size of the generator component increases the complexity of the S-ICD implantation, may cause the patient discomfort post-implantable, and/or may induce body dysmorphic feelings in the patient.

Another drawback of some known S-ICD systems is that the subcutaneous leads may not sufficiently conform to the shape of the patient body at the implant site to permit a normal range of motion without discomfort. For example, the subcutaneous leads, or at least the shocking coils thereof, may be relatively rigid and may cause pain or at least discomfort as the patient moves within the normal range of motion. Furthermore, the leads may produce visible protrusions along the skin as the patient moves, which may provoke body dysmorphia issues.

A need remains for implantable medical devices that can achieve satisfactory defibrillation performance without intra-cardiac and/or transvenous leads and with a smaller generator than known subcutaneous IMDs. A need remains for subcutaneous leads that conform to the shape of the patient's body without causing discomfort during the normal range of motion.

SUMMARY

In accordance with an embodiment, a lead for an implantable medical device (IMD) is provided that includes an electrode. The electrode has a plurality of brick segments that are discrete and mechanically connected to one another in a line. The brick segments are electrically conductive and electrically connected to one another. The brick segments are configured to be powered by a pulse generator of the IMD to deliver high-voltage shocks for defibrillation therapy.

Optionally, the lead includes a lead body configured to be mechanically and electrically connected to the pulse generator and the electrode such that the lead body extends from the pulse generator to the electrode.

The electrode may include one or more support cables. Each of the one or more support cables extends along the brick segments and affixes to the brick segments to secure the brick segments to one another in the line. The one or more support cables may be electrically conductive and may provide an electrically conductive pathway between the brick segments. Each of the brick segments may define a hollow cavity through a respective body of the brick segment. The hollow cavities of the brick segments may align to form a central channel of the electrode. The one or more support cables may be disposed within the central channel and affix to interior surfaces of the bodies of the brick segments. Each of the brick segments may have a body that has an oblong shape with first and second lateral portions. The body may define grooves or apertures through a length of the body at the first and second lateral portions. The grooves or apertures may be configured to receive the one or more support cables therein.

Optionally, adjacent brick segments in the line are mechanically connected to one another at joints via pins that extend through the corresponding adjacent brick segments. Optionally, each brick segment longitudinally extends from a first end of the brick segment to a second end of the brick segment opposite the first end. The first end of a first brick segment may nest within the second end of a second brick segment that is adjacent to the first brick segment along the line to form a joint. The first brick segment may be pivotable relative to the second brick segment at the joint. Optionally, the brick segments include a first end piece at a proximal end of the electrode, a second end piece at a distal end of the electrode, and a plurality of middle pieces between the first and second end pieces in the line. The middle pieces may have a same size and shape as one another. Each of the brick segments may have an oblong cross-sectional shape. Optionally, the electrode is a first electrode and the lead includes a second electrode configured to provide second high-voltage shocks for the defibrillation therapy. The second electrode may be disposed, along a length of the lead, between the first electrode and a proximal end of the lead. The proximal end is configured to connect to the pulse generator of the IMD.

In accordance with an embodiment, a method of producing a lead for an implantable medical device (IMD) is provided. The method includes forming an electrode by mechanically connecting a plurality of brick segments to one another in a line. The brick segments are discrete, electrically conductive, and electrically connected to one another. The brick segments are configured to be powered by a pulse generator of the IMD to deliver high-voltage shocks for defibrillation therapy.

Optionally, the method includes securing a lead body to the electrode and electrically connecting the lead body to the electrode. The lead body is configured to convey power from the pulse generator to the electrode for the defibrillation therapy. Optionally, forming the electrode may include affixing one or more support cables, that extend along the brick segments, to the brick segments to secure the brick segments one another in the line. The method may include welding the one or more support cables to the brick segments. Alternatively, the method may include crimping the brick segments onto the one or more support cables to affix the one or more support cables to the brick segments. Optionally, each brick segment longitudinally extends from a first end of the brick segment to a second end of the brick segment opposite the first end. Forming the electrode may include nesting the first end of a first brick segment within the second end of a second brick segment that is adjacent to the first brick segment along the line to form a joint. Each of the brick segments may have an oblong cross-sectional shape. Optionally, the method includes implanting the lead such that the electrode is disposed in a subcutaneous location within the patient.

In accordance with an embodiment, an implantable medical device (IMD) is provided that includes a pulse generator and a lead. The lead includes a lead body and an electrode. The lead body is mechanically and electrically connected to both the pulse generator and the electrode, and extends from the pulse generator to the electrode. The electrode includes a plurality of brick segments that are discrete and mechanically connected to one another in a line. The brick segments are electrically conductive and electrically connected to one another. The pulse generator is configured to power the brick segments of the electrode, via the lead body, to deliver high-voltage shocks for defibrillation therapy.

BRIEF DESCRIPTION OF THE DRAWINGS

FIG. 5 is a flow chart of a method for producing an implantable medical device (IMD) according to an embodiment.

FIG. 16 is a flow chart of a method for producing a lead for an implantable medical device (IMD) according to an embodiment.

FIG. 18 is a flow chart of a method for implanting a subcutaneous lead of an IMD according to an embodiment.

DETAILED DESCRIPTION

Figure 1:
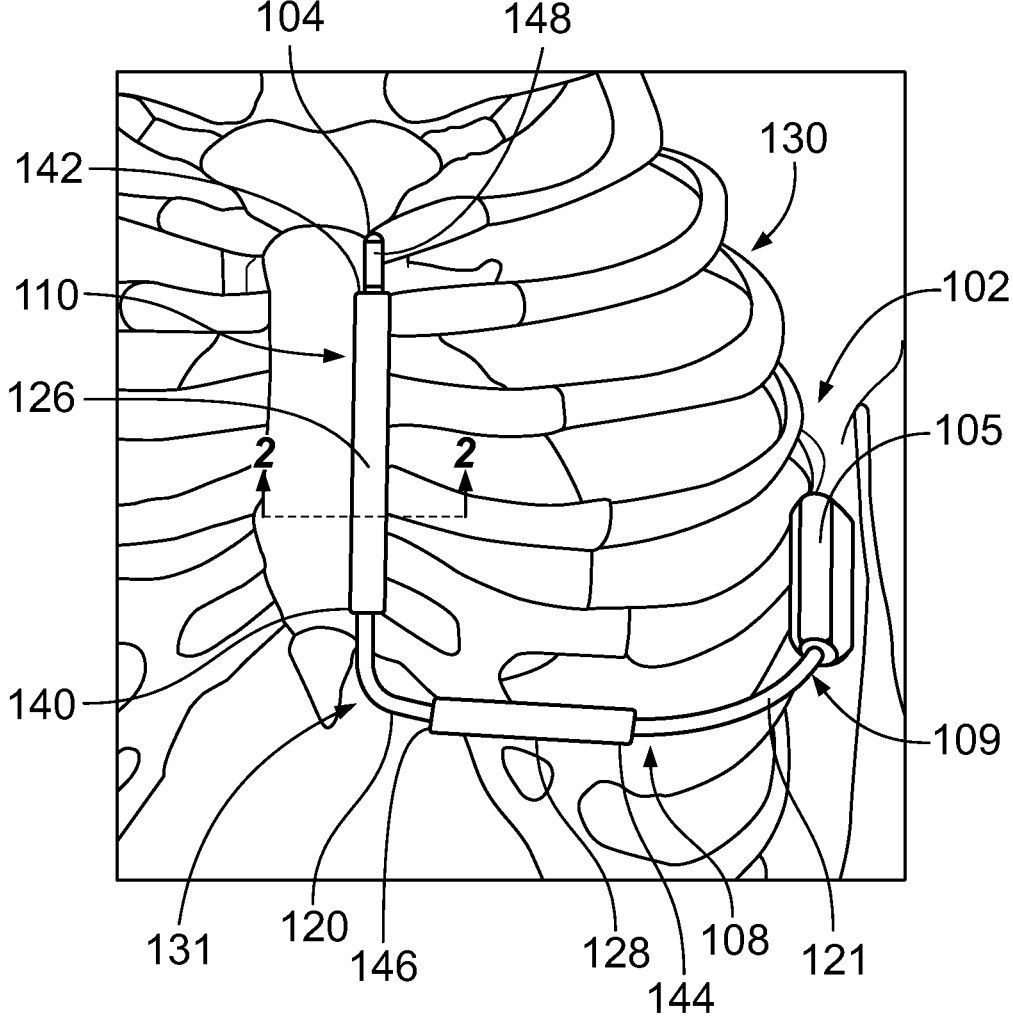
FIG. 1 illustrates a graphical representation of an implantable medical device (IMD) that is configured to apply defibrillation therapy in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Embodiments may be implemented in connection with one or more implantable medical devices (IMDs). Non-limiting examples of IMDs include one or more of neuro-stimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference.

Additionally or alternatively, the IMD may be a subcutaneous IMD (e.g., a S-ICD) that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

All references, including publications, patent applications and patents, cited herein are hereby incorporated by reference to the same extent as if each reference were individually and specifically indicated to be incorporated by reference and were set forth in its entirety herein.

Terms

The terms "cardiac activity signal", "cardiac activity signals", "CA signal" and "CA signals" (collectively "CA signals") are used interchangeably throughout to refer to measured signals indicative of cardiac activity by a region or chamber of interest. For example, the CA signals may be indicative of impedance, electrical or mechanical activity by one or more chambers (e.g., left or right ventricle, left or right atrium) of the heart and/or by a local region within the heart (e.g., impedance, electrical or mechanical activity at the AV node, along the septal wall, within the left or right bundle branch, within the purkinje fibers). The cardiac activity may be normal/healthy or abnormal/arrhythmic. An example of CA signals includes EGM signals. Electrical based CA signals refer to an analog or digital electrical signal recorded by two or more electrodes, where the electrical signals are indicative of cardiac activity. Heart sound (HS) based CA signals refer to signals output by a heart sound sensor such as an accelerometer, where the HS based CA signals are indicative of one or more of the S1, S2, S3 and/or S4 heart sounds. Impedance based CA signals refer to impedance measurements recorded along an impedance vector between two or more electrodes, where the impedance measurements are indicative of cardiac activity.

The terms "high-voltage shock" and "HV shock" refer to defibrillation stimulus delivered at an energy level sufficient to terminate a defibrillation episode in a heart, wherein the energy level is defined in Joules to be 40 J or more and/or the energy level is defined in terms of voltage to be 750V or more.

The term "defibrillation threshold" and acronym "DFT" refer to a minimum amount of energy needed to be delivered in a high-voltage shock of defibrillation therapy in order to return a heart to a normal rhythm from a condition in which the heart is experiencing a fibrillation dysrhythmia episode.

The term "oblong" as used herein refers to elongated shapes that are longer in at least one dimension than another dimension, such that the oblong shapes are not circular/cylindrical or square/cubic. The longest dimension of a cross-sectional shape is referred to herein as a "major dimension," and a shorter dimension of the cross-sectional shape is referred to as a "minor dimension." The minor dimension may be perpendicular to the major dimension.

The terms "processor," "a processor", "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

The term "subcutaneous" shall mean below the skin, but not intravenous. For example, a subcutaneous lead and/or electrode is not located in a chamber of the heart, in a vein on the heart, or in the lateral or posterior branches of the coronary sinus. A subcutaneous lead and/or electrode may be located between the skin and the rib cage, or within an intercostal area between two ribs of the rib cage. The rib cage collectively refers to the ribs, sternum, and thoracic vertebrae. Subcutaneous placement is external of (and does not include) the substernal space, where the substernal space is defined between the undersurface of the rib cage and the pericardium or outer portion of the heart.

FIG. 1 illustrates a graphical representation of an implantable medical device (IMD) 102 that is configured to apply defibrillation therapy in accordance with embodiments herein. The IMD 102 in the illustrated embodiment is a subcutaneous implantable medical device (SIMD) that is configured to be implanted in a subcutaneous area exterior to the heart. The SIMD 102 includes a pulse generator 105 and at least one lead 120 that is operably coupled to the pulse generator 105. The "at least one lead" is hereinafter referred to as "the lead." Nevertheless, it should be understood that the term, "the lead," may mean only a single lead or may mean more than one single lead. The lead 120 includes a lead body 121 that is mechanically connected to the pulse generator 105 and extends from the pulse generator 105 to a distal tip 104 of the lead 120.

The pulse generator 105 includes a housing that contains power circuitry and energy storage devices for generating high-voltage shocks (HV shocks) for defibrillation therapy. The housing may be electrically conductive to form or constitute an electrode utilized to deliver the HV shocks. The electrode associated with the housing of the pulse generator 105 is referred to as the "CAN" electrode. The pulse generator 105 may be subcutaneously implanted within a pocket at a mix-axillary position along a portion of the rib cage 130 of the patient.

The lead 120 may be subcutaneously implanted. In particular embodiments, the SIMD 102 is an entirely or fully subcutaneous SIMD. The SIMD may not include a transvenous lead. The lead 120 in the illustrated embodiment includes a first or proximal segment 108 that extends from the pulse generator 105 along an inter-costal area between ribs. The lead 120 has a proximal end 109 that mechanically couples to the pulse generator 105, and electrically connects to the pulse generator 105 to establish conductive path(s) to the electrodes of the lead 120. The proximal segment 108 may be laterally oriented to extend along an anterior axillary area of the rib cage 130. The lead 120 has a second or distal segment 110 that extends from the proximal segment 108 to the distal tip 104. The distal segment 110 may extend along the sternum (e.g., over the sternum or parasternally within one to three centimeters from the sternum). The intersection between the distal and proximal segments 108, 110 may be located proximate to the xiphoid process of the patient.

The lead 120 includes at least one electrode that is electrically connected to the pulse generator 105 and delivers the HV shocks for defibrillation therapy. In the illustrated embodiment, the lead 120 has a first or primary electrode 126 disposed along the distal segment 110 and a second or secondary electrode 128 disposed along the proximal segment 108. The electrodes 126, 128 may be referred to as shocking electrodes. The electrodes 126, 128 may be elongated coil electrodes. The lengths of the coil electrodes 126, 128 may be in a range from about 3 cm to about 10 cm. In the illustrated embodiment, the primary electrode 126 is longer than the secondary electrode 128. For example, the primary electrode 126 may be about 8 cm, and the secondary electrode 128 may be above 5 cm. In an embodiment, when the pulse generator 105 generates a HV shock, the pulse generator 105 supplies electrical power to both of the electrodes 126, 128. Both electrodes 126, 128 may deliver the HV shocks based on the received electrical power. The electrodes 126, 128 may concurrently deliver the HV shocks to different target areas of the heart.

The electrode 126, 128 are spaced apart from each other along the length of the lead 120 by a gap segment 131 of the lead body 121. The gap segment 131 may be proximate to the xiphoid process. The primary electrode 126 may be positioned along an anterior region of the chest, and the secondary electrode 128 may laterally extend between the primary electrode 126 and the pulse generator 105. The electrodes 126, 128 may be subcutaneously positioned at a level that aligns with the heart of the patient for providing a sufficient amount of energy for defibrillation.

The primary electrode 126 may be oriented transverse to an orientation of the secondary electrode 128 when in the implanted position as shown in FIG. 1. For example, the primary electrode 126 has a first orientation extending from a proximal end 140 of the electrode 126 to a distal end 142 of the electrode 126 (defined along the length of the lead 120 relative to the pulse generator 105). The first orientation may be generally parallel to the midsternal line of the patient. The secondary electrode 128 has a second orientation extending from a proximal end 144 of the electrode 128 to a distal end 146 of the electrode 128. The second orientation may be transverse to the first orientation. Optionally, the orientation of the secondary electrode 128 may define an angle between about 60 degrees and 120 degrees (e.g., such as 70 degrees to 110 degrees) relative to the orientation of the primary electrode 126. Due to the orientation, the lead 120 may be referred to as an L-shaped lead. The primary electrode 126 may be referred to as a parasternal electrode. The secondary electrode 128 may be referred to as a transverse electrode.

In an alternative embodiment, the SIMD 102 may lack the secondary electrode 128. For example, the proximal segment 108 may not have any shocking electrodes. The primary electrode 126 may be the only shocking electrode on the lead 120 that delivers the HV shocks supplied from the pulse generator 105.

Optionally, the lead 120 may include one or more sensing electrodes 148 to detect far field electrogram signals. The sensing electrode(s) 148 may collect subcutaneous cardiac activity (CA) signals in connection with multiple cardiac beats. In the illustrated embodiment, one sensing electrode 148 is disposed at the distal tip 104 of the lead 120. The SIMD 102 may process the CA signals to detect arrhythmias, such as ventricular tachycardia and/or atrial fibrillation. If an arrhythmia is detected, the SIMD 102 may automatically take one or more actions depending on characteristics of the arrythmia, such as type and severity. The actions may include delivering one or more electrical HV shocks (e.g., shock pulses) via the shocking electrodes 126, 128 in an attempt to achieve cardioversion. Optionally, another IMD may be implanted within the heart, such as a leadless pacemaker. The SIMD 102 may be configured to communicate with the other intra-cardiac IMD. For example, the intra-cardiac IMD may signal to the SIMD 102 when an arrythmia is detected for the SIMD 102 to deliver the HV shocks in response to receiving the signal.

The SIMD 102 according to the embodiments described herein can achieve satisfactory defibrillation performance without intra-cardiac and/or transvenous leads and with a smaller generator than known subcutaneous IMDs. For example, the SIMD 102 may achieve enhanced shocking energy efficiency by lowering the impedance of the shocking electrodes 126, 128 that deliver the HV shocks into the patient tissue. For example, according to Ohm's law (I=V/ R), reducing the impedance (R) enables the SIMD 102 to achieve a designated current (I) output at a reduced voltage (V) level from the pulse generator 105. The designated current output may be associated with the defibrillation threshold (DFT) of the patient. The DFT refers to the shock energy necessary to achieve cardioversion (e.g., to return a heart to a normal rhythm from a condition in which the heart is experiencing a fibrillation dysrhythmia episode). Reducing the impedance enables the SIMD 102 to deliver HV shocks at or above the DFT at a lower input voltage level, so the cardioversion is more efficient. Even if the current voltage level provides output current at or above the DFT, reducing the impedance while maintaining a constant voltage may still be beneficial because the output current increases, which enlarges the safety margin to ensure defibrillation is achieved by the shock pulses.

A significant benefit of reducing the impedance is the option to reduce the size and/or power of the pulse generator 105. For example, due to lower impedance the SIMD 102 may be able to provide the same defibrillation therapy at substantially less voltage provided by the pulse generator 105. The pulse generator 105 according to one or more embodiments may have a smaller volume than known SIMDs that provide HV shocks. In an embodiment, the volume of the pulse generator 105 (e.g., the housing) may be less than 50 cm³. For example, the volume of the pulse generator 105 may be less than 40 cm³, such as cm³. The pulse generator 105 may have fewer and/or smaller energy storage devices (e.g., capacitors, battery cells, etc.) than the known SIMDs and/or may have fewer and/or smaller power electronics. In an embodiment, the pulse generator 105 supplies electrical power for the HV shocks at a voltage of less than 1000 V. For example, the SIMD 102 may be able to achieve a clinically acceptable safety margin at voltages less than 900 V, such as less than 850 V. The mass of the pulse generator 105 may be less than 100 grams, such as less than 80 grams.

The relatively small size and weight of the pulse generator 105 may alleviate some patient discomfort experienced with known SIMDs. Furthermore, the pulse generator 105 may be less noticeable to the patient when implanted, which may help avoid body dysmorphia issues. Furthermore, even if the size and/or power capability of the pulse generator 105 is kept similar to the known SIMDs, the increased efficiency may increase the operational lifetime of the SIMD 102 and/or reduce the charge frequency relative to known SIMDs.

The reduction in the impedance may be achieved, at least in part, by the lead 120. For example, at least one of the shocking electrodes 126, 128 may be formed with a modified size and/or shape to reduce the impedance. Clinical trials have experimentally demonstrated that the impedance can be reduced by one or more of (i) increasing the size of the shocking coil(s) along one or more dimensions; (ii) forming the cross-sectional shape of the shocking coil(s) as oblong; and/or (iii) using multiple shocking coils to deliver the HV shocks, such as the two electrodes 126, 128 shown in FIG. 1.

The subcutaneous lead 120, when implanted, may be surrounded at least in part by fat tissue (e.g., lipids) of the patient. The fat may be within adipose tissue, which is adjacent to a fascia layer. Clinical trials have experimentally demonstrated that fat surrounding the electrode(s) increases the impedance relative to the electrode(s) only being surrounded by non-fat tissue in the fascia and/or muscle layers. It has also been observed that fat around the electrode(s) makes the impedance particularly sensitive to electrode cross-sectional size. For example, at tested electrode diameters from 7 F to 11 F implanted within a thin layer of fat, the observed relation was a reduction in impedance of between 6 and 9 ohms for each additional French unit of diameter. As such, larger diameter electrodes experienced lower shocking impedance in the fat than smaller diameter electrodes. With respect to an L-shaped, dual electrode lead 120 as shown in FIG. 1, the inventors have experimentally observed a reduction of 8 ohms per each additional French. The effects of the surrounding tissue on impedance is typically ignored in known systems that use transvenous leads because blood and cardiac tissue have little effect on shocking impedance.

In an embodiment, at least one of the shocking electrodes 126, 128 of the lead 120 has an increased size. That shocking electrode 126, 128 may have an oblong cross-sectional area with a major dimension that is at least 10 F (3.33 mm). The major dimension represents the largest or broadest dimension of the cross-sectional area. For example, if the electrode is cylindrical, the major dimension is equivalent to the diameter. The cross-sectional area may include both the major dimension and a minor dimension that is perpendicular (i.e., orthogonal) to the major dimension. The minor dimension is smaller/narrower than the major dimension. The minor dimension represents the smallest or narrowest dimension of the cross-sectional area, which is perpendicular to the major dimension. The size of the shocking coil is formed with a major dimension of at least 10 F in order to achieve a low shocking impedance and maintain a low DFT, even in the presence of fat.

Figure 2A:
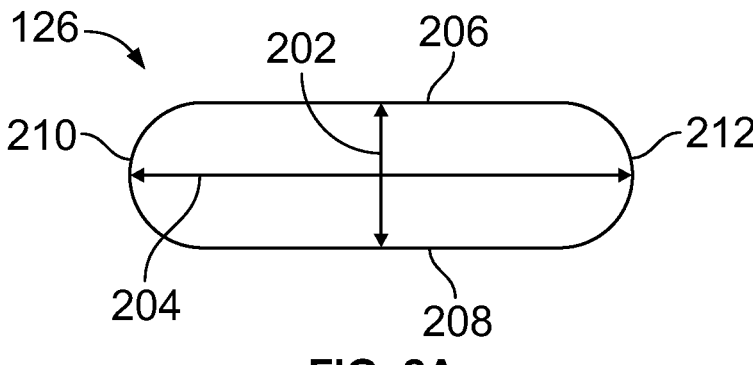
FIG. 2A illustrates a cross-sectional shape of the primary electrode according to a first embodiment.
Figure 2B:
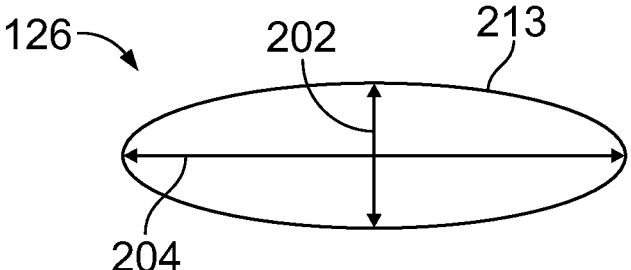
FIG. 2B illustrates the cross-sectional shape of the primary electrode according to a second embodiment.
Figure 2C:
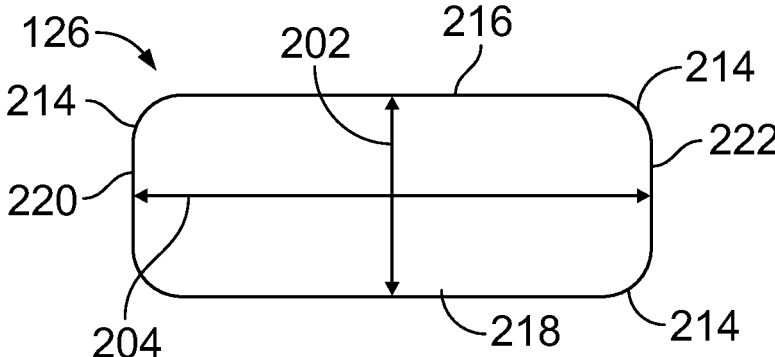
FIG. 2C illustrates the cross-sectional shape of the primary electrode according to a third embodiment.
Figure 2D:
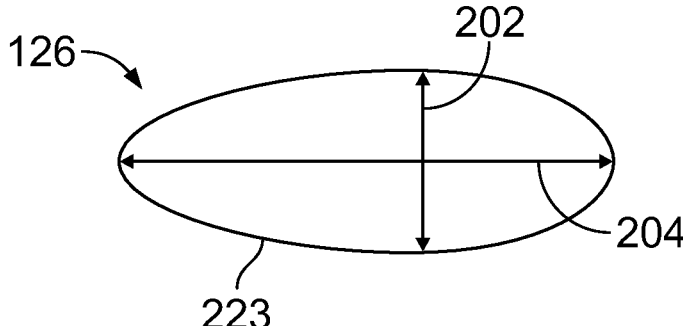
FIG. 2D illustrates the cross-sectional shape of the primary electrode according to a fourth embodiment.

The oblong cross-sectional shape may reduce the shocking impedance. FIG. 2A illustrates a cross-sectional shape of the primary electrode 126 according to a first embodiment. FIG. 2B illustrates the cross-sectional shape of the primary electrode 126 according to a second embodiment. FIG. 2C illustrates the cross-sectional shape of the primary electrode 126 according to a third embodiment. FIG. 2D illustrates the cross-sectional shape of the primary electrode 126 according to a fourth embodiment. The cross-sections in FIGS. 2A-D may be taken through the primary electrode 126 along line 2-2 in FIG. 1. For example, the cross-sectional shapes described herein are cross-sections taken along a plane that is orthogonal to a tangential length direction of the lead 120 at the location of the cross-section. The illustrations in FIGS. 2A-D depict the perimeter shape (e.g., form) of the electrode 126 without showing the conductive elements of the lead 120 and/or electrode 126 within the area defined by the perimeter shapes. Each of the oblong cross-sectional shapes in FIGS. 2A-D has a respective minor dimension 202 and a respective major dimension 204. The minor dimension 202 may represent a thickness of the electrode 126, and the major dimension 204 represents a width of the electrode 126. The major dimension 204 is greater than the minor dimension 202. In an embodiment, the major dimension 204 is at least 10 F (3.33 mm).

The primary electrode 126 in FIG. 2A has a shape referred to herein as a racetrack. The electrode 126 has a first planar side 206 and a second planar side 208. The thickness of the electrode (e.g., the minor dimension 202) is defined between the first and second planar sides 206, 208. The planar sides 206, 208 may be parallel to each other. The electrode 126 has a first curved side 210 and a second curved side 212. Each of the curved sides 210, 212 extends from the first planar side 206 to the second planar side 208. The width of the electrode (e.g., the major dimension 204) is defined between the first and second curved sides 210, 212. In an embodiment, the curved sides 210, 212 have a radius of curvature that is half of the thickness of the electrode 126 (e.g., the diameter of the curvature is equal to the electrode thickness). The curved sides 210, 212 may have a different radius in other embodiments.

The primary electrode 126 in FIG. 2B has an oval cross-sectional shape in the form of an ellipse. For example, the perimeter of the elliptical electrode 126 has only curved sides 213; no planar surfaces. The perimeter may be traced by a point moving in a plane so that the sum of its distances from two focal points is constant.

The primary electrode 126 in FIG. 2C has a rectangular cross-sectional shape with rounded corners 214. For example, the electrode has two broad sides 216, 218 spaced apart from each other to define the thickness (e.g., minor dimension 202), and two narrow sides 220, 222 spaced apart from each other to define the width (e.g., major dimension 204). The broad sides 216, 218, and the narrow sides 220, 222 may be planar. The corners 214 are located at the intersections between the sides 216, 218, 220, 222. The corners 214 are curved to avoid snagging on patient tissue and/or implant tools.

The primary electrode 126 in FIG. 2D has an oval cross-sectional shape that is not an ellipse. For example, unlike the ellipse in FIG. 2B that has symmetry along both the minor dimension 202 and the major dimension 204, the oval electrode 126 in FIG. 2D has symmetry only along the major dimension 204. The oval electrode 126 has only curved sides 223 like the ellipse in FIG. 2B.

Although four oblong shapes are shown in FIGS. 2A-2D, the shocking electrodes may have a different oblong cross-sectional shape in other embodiments. For example, the electrode 126 may have a trapezoidal cross-sectional shape with rounded corners. Relative to the rectangular shape in FIG. 2C, the trapezoidal shape may be achieved by forming the first broad side 216 to be shorter than the opposite, second broad side 218, such that the narrow sides 220, 222 angle towards each other and are not parallel.

The following description may refer to any of the electrodes 126 shown in FIGS. 2A-D. The major dimension 204 is greater than the minor dimension 202. The minor dimension 202 (e.g., the thickness) may be at least 3 F (1 mm). When the thickness is less than 3 F, the impedance may be undesirably high, as observed through experimentation. The cross-sectional area of the electrode 126 may be at least 64 $F^2$ (e.g., at least 7.1 $mm^2$). In an embodiment, the minor dimension is at least 10 F, so the major dimension 204 is greater than 10 F (e.g., 11 F, 13 F, 15 F, 20 F, 30 F, etc.). For example, the cross-sectional area of the electrode 126 may be at least 80 $F^2$ (e.g., at least 9 $mm^2$).

In an embodiment, the cross-sectional shape of the shocking electrode 126 has an aspect ratio of the major dimension 204 to the minor dimension 202 that is at least 2:1. For example, the shape of the oblong electrode 126 may be at least twice as wide as the electrode 126 is thick. The minor dimension 202 of the electrode 126 cross-sectional shape may be 8 F, and the major dimension 204 is at least 16 F. In another example, the minor dimension 202 may be 10 F, and the major dimension 204 is at least 20 F. The inventors have experimentally determined that a 10 F by 20 F elliptical coil electrode 126, as shown in FIG. 2B, may reduce shocking impedance by about 20% relative to a cylindrical coil electrode with a 10 F diameter.

The wide aspect ratio of at least 2:1 may enable the electrode 126 to lay flat when implanted in a channel of the patient. The flat shape may reduce the likelihood of the lead 120 twisting within the channel and/or deviating from an installed position. The flat shape may also reduce patient discomfort, as the electrode 126 may be thinner than known cylindrical electrodes. In one or more embodiments, the thickness of the electrode 126 may be in a range from 6 F to about 15 F (2 mm to about 5 mm), to retain a relatively thin form. In an example, the electrode 126 has a thickness of 12 F (4 mm) and a width of 24 F (8 mm). Optionally, the aspect ratio may be greater than 2:1, such as 3:1 or 4:1. In one or more embodiments, the width of the electrode 126 may be in a range from 20 F to about 50 F (6.66 mm to about 16.66 mm).

In an embodiment, the dual-electrode L-shaped lead 120 shown in FIG. 1 can be implanted via a single incision site near the xiphoid process. The proximal segment 108 may be loaded along a first channel that laterally extends from the incision site to the subcutaneous pocket that contains the pulse generator 105 for connecting to the pulse generator 105. The distal segment 110 may be loaded along a parasternal channel that extends from the incision site. Optionally, sutures may be applied to secure the lead 120 to the surrounding tissue and retain the lead 120 in the implanted position.

In an experimental example, it was determined that a subcutaneous lead according to known SIMDs with a single parasternal coil electrode having a cylindrical shape with a 9 F diameter experienced a shocking impedance of about ohms. Modifying the shape and size of the single parasternal coil electrode to have the racetrack shape as shown in FIG. 2A with a thickness of 10 F and a width of 30 F resulted in an impedance reduction. Furthermore, coupling a second coil electrode with that racetrack-shaped coil electrode to provide the L-shaped dual-electrode lead 120 of FIG. 1 resulted in an additional impedance reduction to about 40 ohms (which is 33% less than the 60 ohms achieved using the cylindrical electrode).

In an embodiment, the SIMD 102 includes the dual-electrode lead 120 (as shown in FIG. 1), and the secondary shocking electrode 128 (e.g., transverse electrode) also has an oblong cross-sectional shape. The cross-sectional shape of the secondary electrode 128 may have a major dimension that is at least 10 F (3.33 mm). The cross-sectional shape of the secondary electrode 128 may be any of the shapes shown in FIGS. 2A-2D. The two electrodes 126, 128 may have the same cross-sectional shape and sizes. For example, both electrodes 126, 128 may have the same racetrack shape as shown in FIG. 2A with the same dimensions.

In an embodiment, portions of the lead body 121 outside of the electrodes 126, 128 may have cylindrical cross-sectional shapes. The cylindrical shapes may assist with bending and twisting the lead 120 during implant, such as to achieve the desired L-shaped bend at the gap segment 131 between the electrodes 126, 128. The cylindrical lead body 121 may have a smaller diameter than the major dimensions of the electrodes 126, 128. Optionally, the cross-sectional shape of the lead body 121 may be oblong and consistent with the shape of the electrodes 126, 128, such that the lead 120 is approximately uniform along the length.

In a first alternative embodiment, the secondary electrode 128 may have a different oblong shape than the primary electrode 126. For example, the secondary electrode 128 may have the rectangular shape in FIG. 2C, and the primary electrode 126 may have the racetrack shape, an oval (e.g., elliptical) shape, a trapezoidal shape, or the like. In a second alternative embodiment, the primary and secondary electrodes 126, 128 may have different dimensions. For example, the primary electrode 126 may be wider than the secondary electrode 128, even if the two electrodes have the same oblong cross-sectional shape. In an example application, the primary electrode 126 may be 3 mm (9 F) thick and 10 mm (30 F) wide, and the secondary electrode 128 may be 3 mm (9 F) thick and 5 mm (15 F) wide. In a third alternative embodiment, the secondary electrode 128 may not have an oblong cross-sectional shape. For example, the secondary electrode 128 may have a cylindrical shape. In a fourth alternative embodiment, the secondary electrode 128 may have the oblong cross-sectional shape, while the primary electrode 126 is cylindrical.

Optionally, one or both of the electrodes 126, 128 that are oblong may include an energy directivity layer along one of the broad surfaces for directing the HV shocks inward towards the thoracic cavity and the heart. For example, the oblong shapes shown in FIGS. 2A-D enable defining one of the broad sides as a heart-facing side and the opposite broad side as a back side. A conductive shield layer and/or an insulator layer may be applied on the back side of the electrodes 126, 128 prior to implant. When implanted, the shield layer and/or insulator layer may serve to focus the shocking energy in a direction towards the thoracic cavity and limit the shocking energy that dissipates in directions away from the thoracic cavity.

During implantation, air that is present within the channel of the patient may surround at least a portion of the shocking electrode(s) 126, 128. The air may increase the shocking impedance by providing insulation between the electrode(s) 126, 128 and the body fluids/tissues. Flushing the body channel(s) with saline or another fluid may exclude trapped air from the channel(s) and provide a more favorable interface for the electrode(s) 126, 128 with reduced shocking impedance. During clinical investigations, it was observed that flushing saline around the shocking electrode(s) can reduce shocking impedance in the range of about 9% to 13% relative to not flushing. Known methods of flushing fluid into dead-end body channels may be messy, may require multiple injections, and/or may not adequately wet the entire length of the shocking electrodes.

Figures 3, 4:
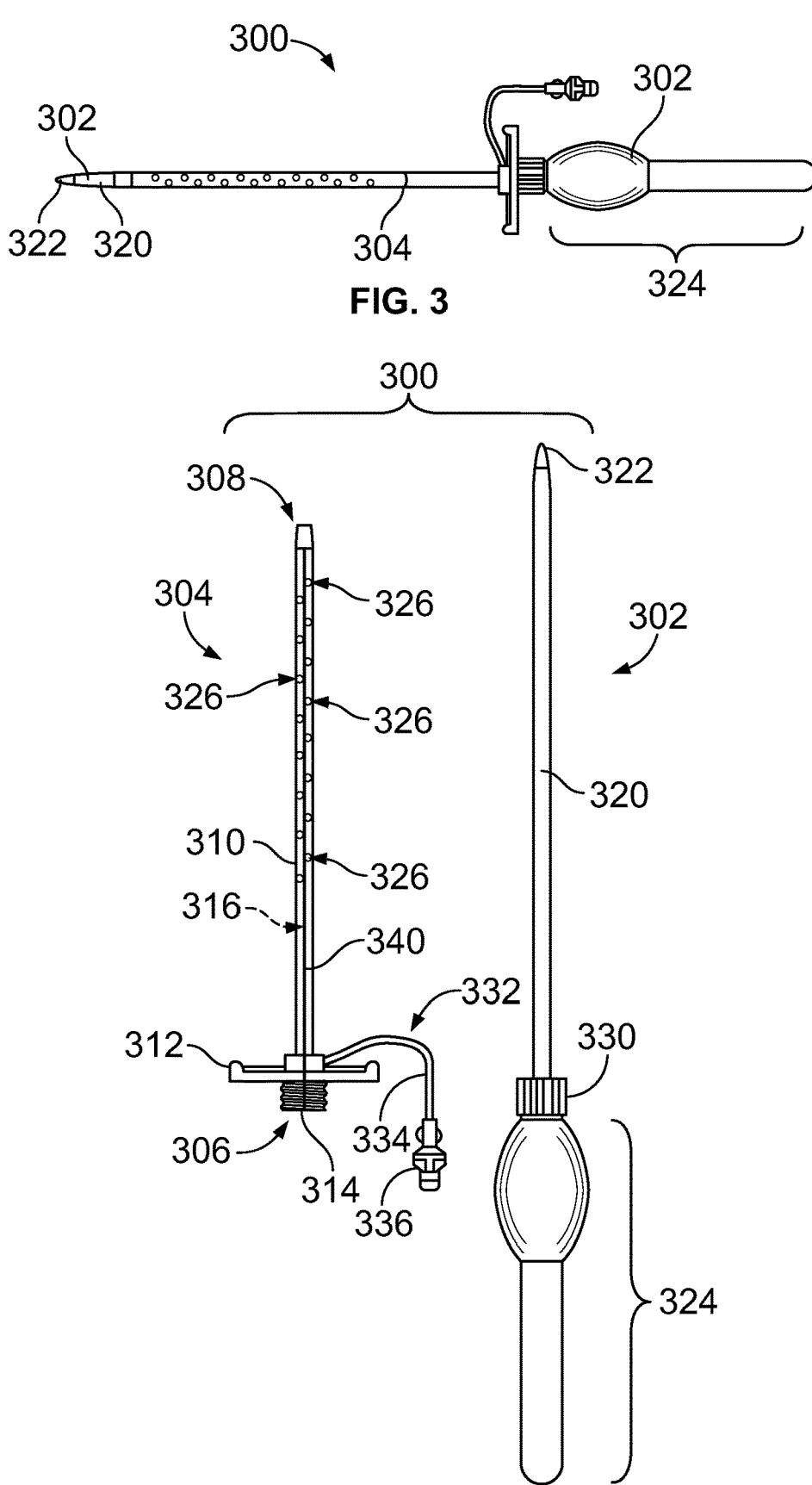
FIG. 3 illustrates an implant tool assembly for implanting a subcutaneous lead according to an embodiment.
FIG. 4 illustrates the implant tool assembly of FIG. 3 in a disassembled state.

FIG. 3 illustrates an implant tool assembly 300 for implanting a subcutaneous lead according to an embodiment. The implant tool assembly 300 may be used to tunnel a subcutaneous channel through a patient, and to introduce a subcutaneous lead into the channel. The subcutaneous lead may be the lead 120 shown in FIG. 1. For example, the implant tool assembly 300 may be used to implant subcutaneous leads that have at least one shocking electrode that has an oblong cross-sectional shape with a major dimension of at least 10 F. The implant tool assembly 300 includes a tunneling tool 302 and an introducer sheath 304. The introducer sheath 304 enables convenient and effective fluid injection for flushing a channel formed by the tunneling tool 302. The fluid that is injected may be a saline solution. The fluid injection may occur prior to introducing the subcutaneous lead 120 into the channel. Alternatively, the lead 120 may be within the sheath 304 and the channel during the fluid injection, such that the flushing occurs with the lead 120 implanted. The sheath 304 is designed to create a fluid (e.g., saline) interface that surrounds the lead 120 and exclude air bubbles from the channel, which reduces the shocking impedance. The implant tool assembly 300 can be used for single incision implants or multi-incision implants.

FIG. 4 illustrates the implant tool assembly 300 in a disassembled state. The introducer sheath 304 is elongated and extends from a proximal end 306 to a distal end 308. The sheath 304 includes a tubular body 310 that is hollow. The sheath 304 includes a gripping element 312 projecting from the tubular body 310. The gripping element 312 may be located at or near the proximal end 306. The gripping element 312 may be a flange, one or more tabs, a ring-shaped handle, or the like. The gripping element 312 provides a feature for the operator (e.g., doctor or technician) to hold onto when manipulating the sheath 304. The sheath 304 defines an internal cavity 316 that extends the length of the sheath 304 from the proximal end 306 to the distal end 308. The sheath 304 defines openings to the internal cavity 316 at both ends 306, 308. The internal cavity 316 is sized and shaped to permit a rod 320 of the tunneling tool 302 to extend through the internal cavity 316. As shown in FIG. 3, when the implant tool is assembled and the rod 320 is within the internal cavity 316, a distal tip 322 of the rod 320 may project beyond the distal end 308 of the sheath 304. A handle segment 324 of the tunneling tool 302 may be adjacent to the proximal end 306 of the sheath 304.

During implantation, the sheath 304 may receive the lead 120 after the tunneling tool 302 is extracted from the sheath 304. The internal cavity 316 is sized and shaped to accommodate the oblong cross-sectional shapes of the shocking electrodes 126, 128 of the lead 120. Optionally, the tubular body 310 may have an oblong cross-sectional shape that matches the cross-sectional shape of one or both shocking electrodes 126, 128. Alternatively, the tubular body 310 may be cylindrical and sized such that the internal diameter of the internal cavity 316 is larger than the major dimension 204 of the electrodes 126, 128.

The introducer sheath 304 includes flushing holes 326 that extend through a wall of the tubular body 310 to fluidly connect the internal cavity 316 to an external environment outside of the sheath 304. The flushing holes 326 may be disposed at different locations along the length of the tubular body 310 between the gripping element 312 and the distal end 306. In the illustrated embodiment, the flushing holes 326, on average, may be located closer to the distal end 306 than to the gripping element 312. The flushing holes 326 may be disposed at different radial locations along the perimeter (e.g., circumference) of the tubular body 310. For example, the flushing holes 326 may be arranged in an array that extends radially and longitudinally along the tubular body 310. The flushing holes 326 may emit the fluid (e.g., saline solution) that is injected into the internal cavity 316 such that the fluid is ejected from the sheath 304 at a different locations and in different directions. Ejecting the fluid at different locations and directions from the sheath 304 may provide more reliable, effective, and/or cleaner establishment of the fluid-electrode interface without air bubbles, relative to ejecting fluid through only the opening at the distal end 306.

In an embodiment, the sheath 304 includes a side-port 332 that is connected to the tubular body 310 proximate to the proximal end 306. The side-port 332 includes a hose 334 that is fluidly connected to the internal cavity 316. In the illustrated embodiment, the hose 334 is connected to the tubular body 310 at a location proximate to the gripping element 312, such as just distal of the gripping element 312 (e.g., between the gripping element 312 and the array of flushing holes 326). The side-port 332 is designed to receive the fluid used to flush the channel of the patient. A distal end of the side-port 332 may include a valve 336 that is coupled to the hose 334. The flushing fluid may be injected through the valve 336. In an embodiment, the valve 336 may be a stop-cock valve with a lure lock to accommodate a syringe that injects the fluid.

The sheath 304 optionally includes a locking element 314 for selectively securing the sheath 304 to the tunneling tool 302. The locking element 314 in the illustrated embodiment is a threaded segment of the tubular body 310. The tunneling tool 302 includes a complementary rotatable threaded nut 330 for threadably coupling to the locking element 314. Alternatively, the locking element 314 may be a bayonet slot, a latch, or the like. The locking element 314 may be located at or near the proximal end 306. The tunneling tool 302 may be locked to the sheath 304 when the implant tool assembly 302 is in the assembled state shown in FIG. 3 and the implant tool assembly 302 is inserted through an incision of the patient to form a channel in the patient. After the channel is formed, the locking element 314 may be uncoupled from the tunneling tool 302 to permit the tunneling tool 302 to be extracted from the sheath 304 and the channel of the patient, while the sheath 304 remains in place within the channel.

The sheath 304 optionally may be splitable. For example, the sheath 304 may define at least one linear seam 340 along all or at least a majority of the length. Each seam 340 represents an area in which the wall thickness is reduced relative to the wall thickness adjacent to the seam 340. After the lead 120 is implanted through the sheath 304 and the channel is flushed, the sheath 304 may be split or divided to enable extracting the sheath 304 without interfering with the positioning of the lead 120. In an embodiment, an operator (e.g., doctor or technician) may pull two parts of the gripping element 312 in opposite directions away from the seam 340 with sufficient force to cause the sheath 304 to split apart at the seam(s) 340. The sheath 304 may split into two parts which can individually be removed from the channel of the patient without dislodging the lead 120. In another embodiment, the sheath 304 may include a cutting element that slits the seam(s) 340 to provide the splitting effect.

The following description refers to an implant procedure of a subcutaneous IMD (SIMD) utilizing the implant tool assembly 300 according to an embodiment. The order of these steps may be rearranged unless not practically possible based on the context of the steps. First, an operator makes a subcutaneous pocket in a sub-axillary area of the patient for accommodating the pulse generator 105. Then, a 2 cm long incision is made in the region of the xyphoid process. The implant tool assembly 300 in the assembled state shown in FIG. 3 is introduced by blunt dissection while the tip 322 of the rod 320 is directed to create a parasternal channel as close as possible to the surface of the fascia about 1 cm to the right and/or left of the xyphoid process.

Once inserted to the desired depth, the tunneling tool 302 is removed, while the sheath 304 remains within the channel. The next step may be saline flushing. A saline-filled syringe may be attached to the valve 336 of the side-port 332 for injection of saline. The operator may cover the opening at the proximal end 306 of the tubular body 310 with a thumb, cork, or cap. Optionally, the sheath 304 may include a hemostasis valve which blocks the opening at the proximal end 306. The saline that is injected into the sheath 304 may be discharged to fill the small cavity remaining at the distal dead-end of the channel and some of the saline is ejected into the rest of the channel through the flushing holes 326 incorporated into the walls of the sheath 304 to uniformly wet the inside of the parasternal channel.

The distal segment 110 of the lead 120 may be inserted into the sheath 304 after the parasternal channel is flushed. After placement of the distal segment 110, the process described above may be essentially repeated to form a transverse channel connecting the parasternal channel to the pocket that houses the pulse generator 105. For example, a second implant tool assembly 300 may be used to form the transverse channel. The second implant tool assembly 300 may be similar to the first implant tool assembly 300 used to form the parasternal channel and implant the distal segment 110 of the lead 120. The tunneling tool 302 of the second assembly used to form the transverse channel may be only slightly different than the one used to form the parasternal channel, such as longer. Following the transverse placement of the second introducer sheath 304 and the extraction of the tunneling tool 302, the transverse channel may be flushed similar to the flushing of the parasternal channel. The proximal segment 108 of the lead 120 may be inserted into the second introducer sheath 304 and the wetted transverse channel. The proximal end 109 of the lead 120 is then connected to the pulse generator 105.

Both the first and second introducer sheaths 304 are removed after implant of the corresponding segments 110, 108 of the lead 120. For example, the sheaths 304 may be splitable (e.g., peelable, slitable, etc.) to enable extracting the sheaths 304 from around the lead 120 with the lead 120 intact. Optionally, both sheaths 304 may be removed after the entire lead 120 is implanted. Alternatively, the first sheath 304 may be removed prior to implanting part of the lead 120. For example, the first sheath 304 may be removed prior to implanting the proximal segment 108 into the transverse channel using the second sheath 304.

FIG. 5 is a flow chart 500 of a method for producing an implantable medical device (IMD) according to an embodiment. The method may include additional steps than shown in FIG. 5, fewer steps than shown in FIG. 5, and/or different steps than shown in FIG. 5. The method is described with reference to the SIMD 102 shown in FIG. 1, although the method may be performed with other leads and IMDs. At step 502, a lead 120 is formed that is configured to be operably coupled to a pulse generator 105. The lead 120 is also configured to be subcutaneously implanted with a patient.

At step 504, an electrode 126 (e.g., a shocking electrode) is secured on the lead 120. The electrode 126 is configured to receive electrical power from the pulse generator 105 and to provide high-voltage shocks for defibrillation therapy for the patient. The electrode 126 has an oblong cross-sectional shape with a major dimension 202 that is at least 10 F. The oblong cross-sectional shape of the electrode 126 may have a major dimension 204 that is greater than the minor dimension 202, and an aspect ratio of the major dimension 204 to the minor dimension 202 may be at least 2:1.

In a first example, the oblong cross-sectional shape of the electrode 126 includes first and second planar sides 206, 208 that are parallel to each other and first and second curved sides 210, 212. Each of the first and second curved sides 210, 212 extends from the first planar side 206 to the second planar side 208. The electrode 126 may have other oblong cross-sectional shapes in other embodiments, such as rectangular with rounded corners or oval (e.g., elliptical, egg-shaped, or the like).

At step 506, a second electrode 128 (e.g., shocking electrode) is secured to the lead 120 at a location (along the lead length) between the first electrode 126 and a proximal end 109 of the lead 120 that connects to the pulse generator 105. Both the first electrode 126 and the second electrode 128 may be configured to provide the high-voltage shocks for the defibrillation therapy.

At step 508, the lead 120 is implanted within the patient. The lead 120 may be implanted such that the first electrode 126 has a first orientation and the second electrode 128 has a second orientation, wherein the first orientation is transverse to the second orientation. For example, the first electrode 126 may be located in a parasternal area of the patient, and the second electrode 128 may laterally extend along an inter-costal area between ribs of the patient. Also at step 508, the pulse generator 105 is separately implanted into a subcutaneous pocket within the patient. The pulse generator 105 may be located at a sub-axillary area of the patient.

At step 510, a proximal end 109 of the lead 120 is mechanically coupled to, and electrically connected to, the pulse generator 105 within the patient to establish a conductive path from the pulse generator 105 to the shocking electrodes 126, 128. In an embodiment, the pulse generator may have a volume less than 50 cm³ and/or may supply electrical power at less than 1000 V to the electrodes 126, 128 to provide the high-voltage shocks.

Figure 6:
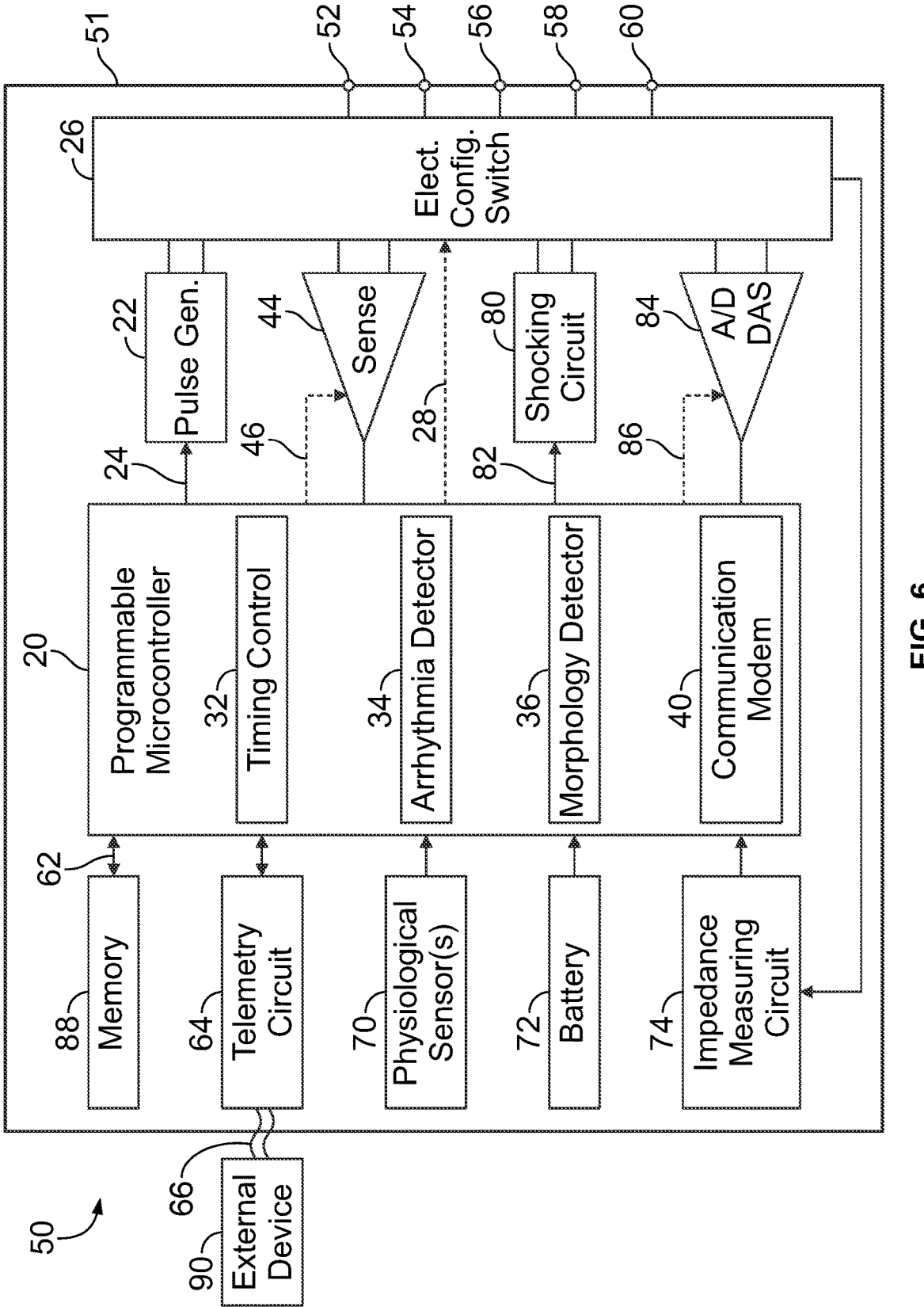
FIG. 6 shows a block diagram of an IMD that is configured to be implanted into a patient.

FIG. 6 shows a block diagram of an IMD 50 that is configured to be implanted into a patient. The IMD 50 may represent the SIMD 102 shown in FIG. 1. The IMD 50 may be implemented to monitor ventricular activity alone, or both ventricular and atrial activity through sensing circuit. The IMD 50 may treat both fast and slow arrhythmias with stimulation therapy, including cardioversion, pacing stimulation, an implantable cardioverter defibrillator, suspend tachycardia detection, tachyarrhythmia therapy, and/or the like.

The IMD 50 has a device case (or housing) 51 to hold the electronic/computing components. The case 51 (which can also be referred to as the "housing," "can," "encasing," or "case electrode") may be programmably selected to function as an electrode for certain sensing modes. Case 51 further includes a connector (not shown) with at least one terminal 52 and optionally additional terminals 54, 56, 58, 60. The terminals may be connected to electrodes that are located in various locations within and about the heart. The type and location of each electrode may vary. For example, the electrodes may include various combinations of ring, tip, coil, shocking electrodes, and the like.

The IMD 50 includes a programmable microcontroller 20 that controls various operations of the IMD 50, including cardiac monitoring and stimulation therapy. Microcontroller 20 includes a microprocessor (or equivalent control circuitry), RAM and/or ROM memory, logic and timing circuitry, state machine circuitry, and I/O circuitry. Microcontroller 20 includes an arrhythmia detector 34 that is configured to cardiac activity data to identify potential AF episodes as well as other arrhythmias (e.g., Tachycardias, Bradycardias, Asystole, etc.).

An electrode configuration switch 26 is optionally provided to allow selection of different electrode configurations under the control of the microcontroller 20. The electrode configuration switch 26 may include multiple switches for connecting the desired electrodes to the appropriate I/O circuits, thereby facilitating electrode programmability. The switch 26 is controlled by a control signal 28 from the microcontroller 20. Optionally, the switch 26 may be omitted and the I/O circuits directly connected to a housing electrode.

The IMD 50 further includes a chamber pulse generator 22 that generates stimulation pulses for connecting the desired electrodes to the appropriate I/O circuits, thereby facilitating electrode programmability. The pulse generator 22 is controlled by the microcontroller 20 via control signals 24. The IMD 50 includes a sensing circuit 44 selectively coupled to one or more electrodes that perform sensing operations through the switch 26 to detect cardiac activity. The sensing circuit 44 may include dedicated sense amplifiers, multiplexed amplifiers, or shared amplifiers. The sensing circuit 44 may operate in a unipolar sensing configuration or a bipolar sensing configuration. The output of the sensing circuit 44 is connected to the microcontroller 20 which, in turn, triggers, or inhibits the pulse generator 22 in response to the absence or presence of cardiac activity. The sensing circuit 44 receives a control signal 46 from the microcontroller 20 for purposes of controlling the gain, threshold, polarization, and timing of any blocking circuitry (not shown) coupled to the sensing circuit.

The IMD 50 further includes an analog-to-digital ND data acquisition system (DAS) 84 coupled to one or more electrodes via the switch 26 to sample cardiac signals across any pair of desired electrodes. The ND DAS 84 is controlled by a control signal 86 from the microcontroller 20.

The IMD 50 is communicatively connected to an external device 90. The external device 90 may communicate with a telemetry circuit 64 of the IMD 50 through a communication link 66. The external device 90 facilitates access by physicians to patient data as well as permitting the physician to review real-time cardiac signals while collected by the IMD 50.

The microcontroller 20 is coupled to a memory 88 by a suitable data/address bus 62. The memory 88 stores the programmable operating parameters used by the microcontroller 20 and/or data associated with the detection and determination of arrhythmias.

The IMD 50 may further include one or more physiologic sensors 70 adjust pacing stimulation rates, detect changes in cardiac output, changes in the physiological condition of the heart, and/or diurnal changes in activity (e.g., detecting sleep and wake states). Examples of physiological sensors 70 might include sensors that, for example, sense respiration rate, pH of blood, ventricular gradient, activity, body movement, position/posture, minute ventilation (MV), and/or the like.

The battery 72 provides operating power to all of the components in the IMD 50. The battery 72 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more).

The IMD 50 further includes an impedance measuring circuit 74, which can be used for many things, including sensing respiration phase. The IMD 50 is further equipped with a communication modem (modulator/demodulator) 40 to enable wireless communication with the external device 90 and/or other external devices.

The IMD 50 includes a shocking circuit 80 controlled by control signals 82 generated by the microcontroller 20. The shocking circuit 80 generates shocking pulses of low (e.g., up to 0.5 joules), moderate (e.g., 0.5-10 joules), or high energy (e.g., 11 to 40 joules), as controlled by the microcontroller 20.

The microcontroller 20 may include other dedicated circuitry and/or firmware/software components, such as a timing control (module) 32 and a morphology detector (module) 36. The timing control 32 is used to control various timing parameters, such as stimulation pulses (e.g., pacing rate, atria-ventricular (AV) delay, atrial interconduction (A-A) delay, ventricular interconduction (V-V) delay, etc.) as well as to keep track of the timing of RR-intervals, refractory periods, blanking intervals, noise detection windows, evoked response windows, alert intervals, marker channel timing, and the like. The morphology detector 36 is configured to review and analyze one or more features of the morphology of cardiac activity signals, such as the morphology of detected R waves to determine whether to include or exclude one or more beats from further analysis.

Figures 7A, 7B, 7C, 7D:
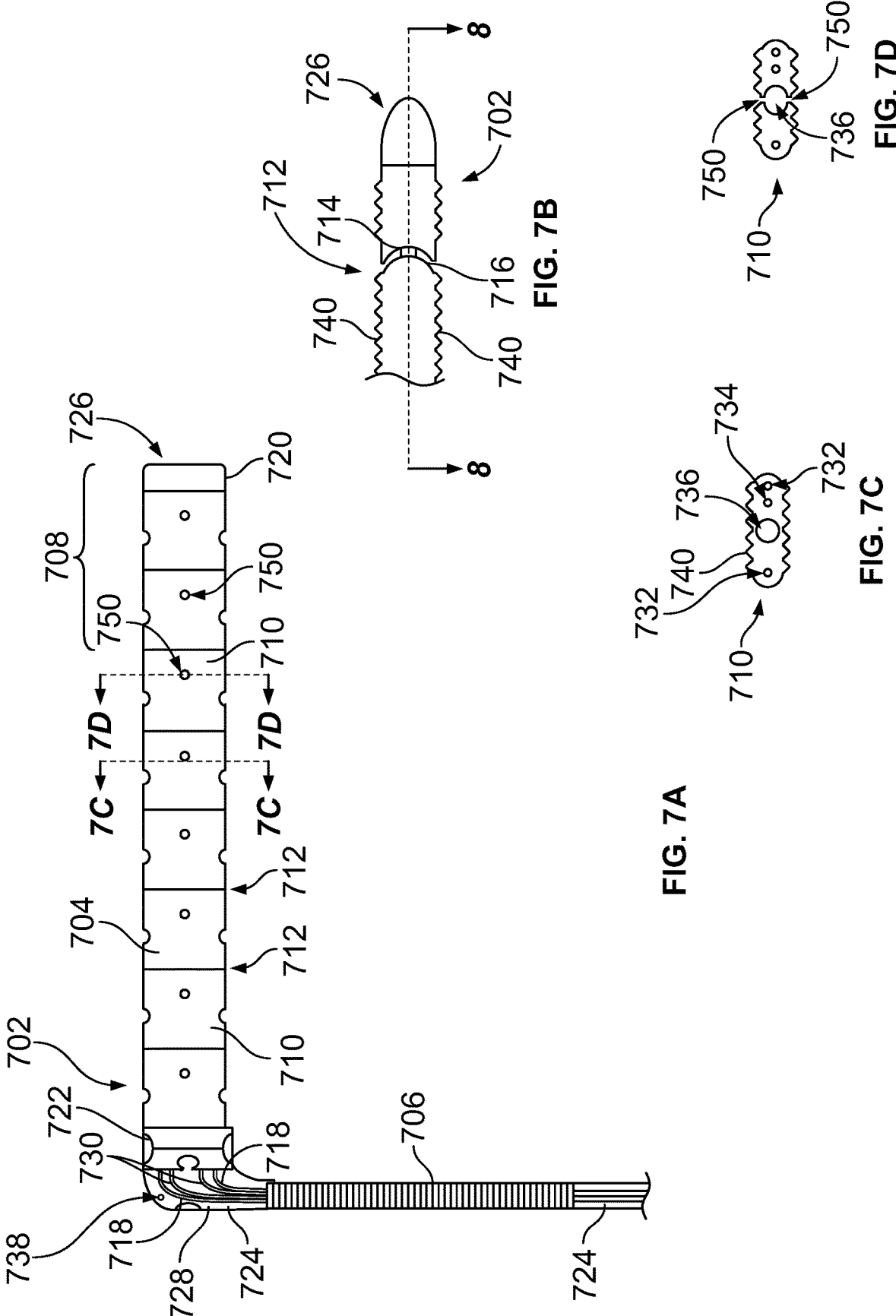
FIG. 7A illustrates a plan view of a lead according to an embodiment.
FIG. 7B is a side view of a distal portion of the lead shown in FIG. 7A.
FIG. 7C illustrates a cross-sectional shape of a brick segment of the lead taken along line 7C-7C in FIG. 7A.
FIG. 7D illustrates a cross-sectional shape of another brick segment of the lead taken along line 7D-7D in FIG. 7A.

FIG. 7A illustrates a plan view of a lead 702 according to an embodiment. The lead 702 may be the lead 120 shown in FIG. 1. The lead 702 includes a primary shocking electrode 704 and a secondary shocking electrode 706. FIG. 7B is a side view of a distal portion 708 of the lead 702 shown in FIG. 7A. In an embodiment, the primary electrode 704 is segmented into plural pieces, referred to herein as brick segments 710. FIG. 7C illustrates a cross-sectional shape of one of the brick segments 710 taken along line 7C-7C in FIG. 7A. FIG. 7D illustrates a cross-sectional shape of another one of the brick segments 710 taken along line 7D-7D in FIG. 7A.

The primary shocking electrode 704 and the secondary shocking electrode 706 optionally may represent the primary shocking electrode 126 and the secondary shocking electrode 128, respectively. For example, the primary electrode 704 may have an oblong cross-sectional shape, as shown in FIGS. 7C and 7D. The secondary electrode 128 may have a cylindrical cross-sectional shape in the illustrated embodiment. In an alternative embodiment, the secondary electrode 128 has an oblong cross sectional shape like the primary electrode 704.

The brick segments 710 are discrete objects. The brick segments 710 may be chicklets, chips, pieces, chunks, tablets, or the like. The brick segments 710 are mechanically coupled together in a line to define the primary electrode 704. The brick segments 710 maybe replicas or copies of one another, such that the brick segments 710 may have the same shapes, dimensions, and features. Each brick segment 710 may have an oblong cross sectional shape. Adjacent brick segments 710 couple together at joints 712. The primary electrode 704 has seams at the joints 712. In an embodiment, as shown in FIG. 7B, the brick segments 710 are nested together at the joints 712. For example, at each joint 712, one of the brick segments 710 has a concave mating surface 714 and the other brick segment 710 has a convex mating surface 716 that nests into the concave mating surface 714. Due to the nesting, the curved surfaces 714, 716 are not visible in the plan view of FIG. 7A. The term "brick segment" refers to how the pieces in aggregate form the electrode 704, without denoting or requiring any specific shape. Thus, the brick segments 710 optionally may not have rectangular prism shapes with planar sides.

The brick segments 710 may be secured together via one or more cables 718 that extend across the joints 712. The cable(s) 718 provide mechanical support for retaining the brick segments 710 in the coupled state as well as the general elongated shape of the electrode 704. The cables 718 are shown in more detail in FIG. 8. The tension of the cable(s) 718 may be adjusted or selected to enable some flexibility of the primary electrode 704 along the joints 712 between brick segments 710. For example, as shown in FIG. 7B, the two brick segments 710 can pivot relative to each other in one dimension (e.g., one degree of freedom) along the nested interface. The flexible characteristic of the primary electrode 704 may beneficially allow the primary electrode 704 to follow a contour of the implant patient's body structure, such as along the contour of the sternum. If a parasternal electrode is not sufficiently flexible, air-filled voids between the lead and the body structure may form during the implant process, which is undesirable. Furthermore, a straight or rigid parasternal electrode that is not able to follow the body contour may cause pain or at least discomfort, and/or may produce visible protrusions along the skin which may provoke body dysmorphia issues.

The lead 702 may include a distal sensing electrode 720 and a proximal sensing electrode 722. The primary electrode 704 may be disposed between the distal and proximal sensing electrodes 720, 722 along the length of the lead 702. The sensing electrodes 720, 722 may collect subcutaneous CA signals in connection with multiple cardiac beats. Each of the sensing electrodes 720, 722 may be secured to the adjacent brick segment 710 next to the respective electrode 720, 722. For example, the sensing electrodes 720, 722 may be chemically bonded to the corresponding brick segments 710 via an epoxy or the like. The sensing electrodes 720, 722 may be electrically insulated from the brick segments 710. The lead 702 may include more or less than two sensing electrodes in an alternative embodiment.

The lead 702 includes a lead body 724 that may extend at least most of the length of the lead 702 from the pulse generator 105 (shown in FIG. 1) to a distal end 726 of the lead 702. The segment of the lead body 724 between the primary electrode 704 and the secondary electrode 706 is a gap segment 131, which is referred to herein as a boot 728. In the illustrated embodiment, the lead 702 is a right angle or L-shaped lead 702, and the boot 728 forms the angled corner. The lead body 724 may be composed of an electrically insulative (e.g., dielectric) material. The insulative material may include silicone rubber, polyurethane, and/or the like. The lead body 724 may be formed by molding (e.g., over-molding, injection molding, etc.) the insulative material. In an embodiment, the insulative material is molded over the cables 718 and one or more electrical wires 730 that connect to the sensing electrodes 720, 722. The insulative material may be molded over a portion of the proximal sensing electrode 722 to mechanically secure the primary electrode 704 to the lead body 724 as the insulative material hardens/solidifies. Optionally, the lead body 724 may be at least partially translucent such that the cables 718 and wires 730 within the boot 728 are visible through the insulative material. Optionally, the boot 728 may define one or more suture openings 738 for receiving a suture to tether the boot 728 to tissue during the implant procedure.

The brick segments 710 may be composed of one or more electrically conductive materials that are safe for human tissue interaction. In an embodiment, the brick segments 710 include one or more metals, such as titanium, nickel, chromium, cobalt, stainless steel, and/or the like. In an example, the brick segments 710 may be formed by machining metal, such that the brick segments 710 are initially formed as solid pieces and then drilling is performed to remove metal material to define the holes shown in FIGS. 7C and 7D. In another example, the brick segments 710 may be formed by a different process, such as molding (e.g., casting). The brick segments 710 of the primary electrode 704 may deliver shock therapy to the patient.

FIG. 7C shows a cross-section of one brick segment 710 along line 7C-7C. The brick segment 710 has an oblong cross-sectional shape. The major dimension may be at least 10 F. Optionally, the minor dimension is at least 10 F. The aspect ratio of the major dimension to the minor dimension may be at least 2:1. The other brick segments 710 in the primary electrode 704 may have the same or a similar construction as the illustrated brick segment 710. The brick segment 710 defines multiple bores therethrough. For example, the brick segment 710 may have one or more cable openings 732 for receiving the cable(s) 718 and one or more wire openings 734 for receiving electrical current-carrying wire(s). In an embodiment, the brick segment 710 also includes a cavity 736 for accommodating an implant tool and/or a flushing solution. The cable(s) 718 and the wire(s) 730 are not shown in FIG. 7C or FIG. 7D.

Optionally, the brick segments 710 may have a non-planar surface texture 740. The non-planar surface texture 740 may include non-planar features, such as ridges, protrusions, undulations, saw teeth, dents, depressions, and/or the like. The features may allow the patient tissue to grow into and grip the features, which secures the electrode 704 in place within the patient, reducing the likelihood of lead migration from the implant position.

Figure 8:
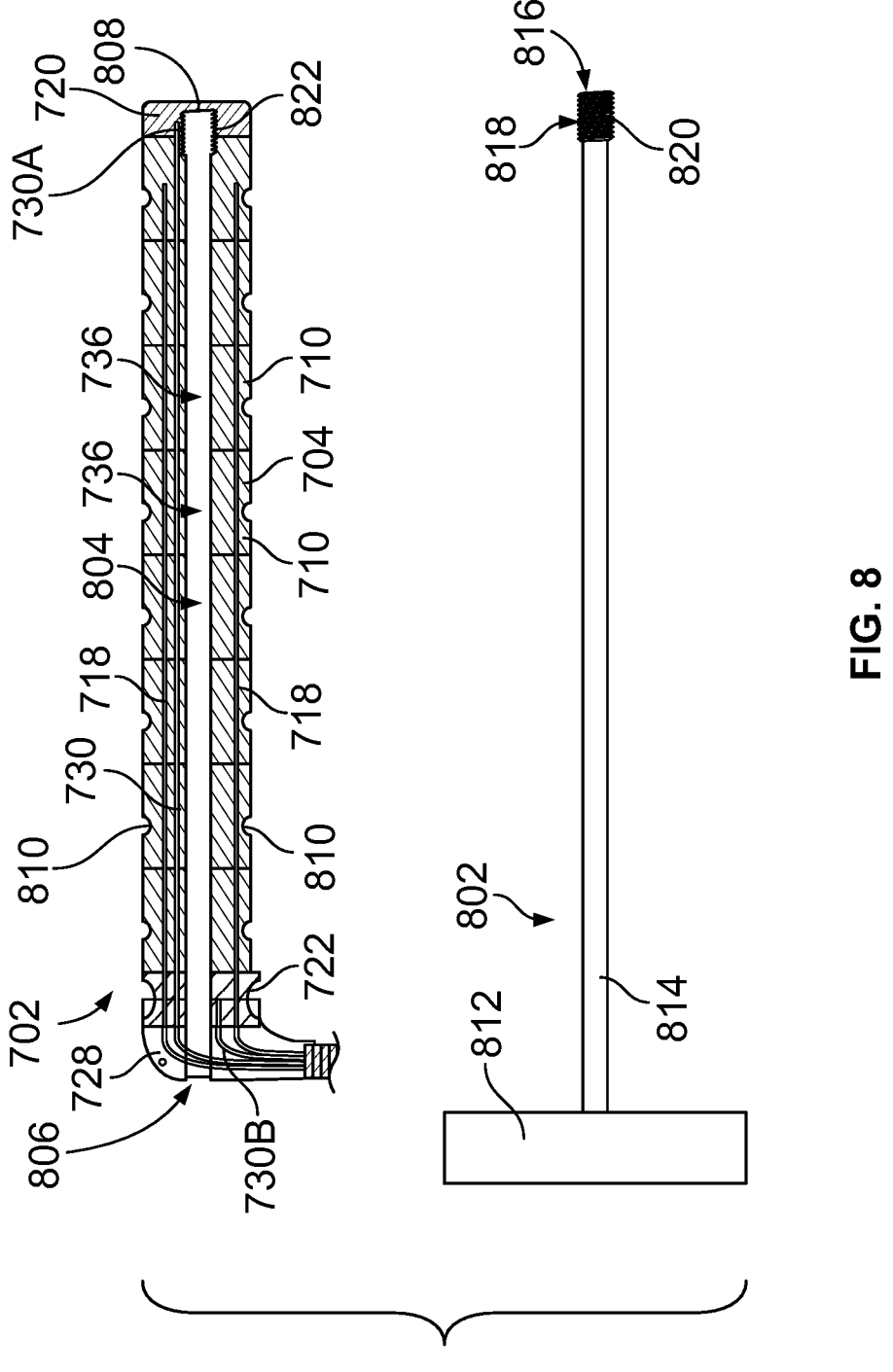
FIG. 8 is a cross-sectional view of a portion of the lead and a plan view of an implant tool according to an embodiment.

FIG. 8 is a cross-sectional view of a portion of the lead 702 and a plan view of an implant tool 802 according to an embodiment. The illustrated portion of the lead 702 includes the sensing electrodes 720, 722, the primary shocking electrode 704, and the boot 728. The cross-section is taken along line 8-8 in FIG. 7B. The lead 702 in the illustrated embodiment has a lumen 804 defined in part by the cavities 736 of the brick segments 710. The lumen 804 continuously extends from an inlet 806 in the boot 728 through the proximal sensing electrode 722, then the brick segments 710, to the distal sensing electrode 720. The distal sensing electrode 720 may include a closed end 808 of the lumen 804. Alternatively, the lumen 804 may extend through a full length of the sensing electrode 720, such that the electrode 720 defines an outlet.

The cables 718 extend through the brick segments 710 to mechanically tether the brick segments 710 together in line. In the illustrated embodiment, two cables 718 are used, and the cables 718 are disposed on opposite sides of the lumen 804. In an embodiment, the cables 718 may be mechanically coupled (e.g., locked) to the brick segments 710 by crimping the brick segments 710 onto the cables 718. For example, each brick segment 710 may be crimped with the cables 718 inside, and the crimp forces may form depressed features 810 in the brick segment bodies. In another embodiment, the cables 718 may be secured (e.g., locked) to the distal-most brick segment 710 that is bonded to the distal sensing electrode 720 and/or to the distal sensing electrode 720 itself, without being secured to one or more of the other brick segments 710. For example, the cables 718 may be secured within the boot 728 in a way that the cables 718 are under tension between the distal brick segment 710 and the boot 728, and the tension maintains the positioning of the brick segments 710. In an alternative embodiment, the same wire and/or cable may be used to convey electric current and provide mechanical retention of the brick segments 710, rather than having two separate elements. For example, the electrical wires 730 that electrically connect to one or more of the electrodes 720, 722, and/or 704 may be used to mechanically couple the brick segments 710 together, such that the lead 702 omits the cables 718.

FIG. 8 shows one electrical wire 730A that extends through the brick segments 710 to the distal sensing electrode 720. A second electrical wire 730B terminates at the proximal sensing electrode 722 without extending through the brick segments 710. The electrical wires 730A, 730B may be insulated wires for electrical insulation from other electrically conductive components, such as the brick segments 710. The lead 702 may include more or less than two electrical wires 730 in other embodiments. For example, the lead 702 may include one or more additional electrical wires 730 that electrically connect to the brick segments 710 for conveying electrical current to power shocking pulses of the primary electrode 704.

In an embodiment, the lead 702 is designed to enable blunt dissection through patient tissue during implant. For example, in contrast to the implant procedure that uses the implant tool assembly 300 shown in FIGS. 3 and 4, the lead 702 may not need to be inserted through a pre-implanted sheath. The lead 702 may be self-implanting. In one example self-implanting application, the lead 702 may not even need a pre-formed channel through the patient formed via a tunneling tool. For example, the lead 702 may be sufficiently rigid and stiff with the implant tool 802 inserted in the lumen 804 that the lead 702 can blunt dissect and form the channel through the patient. The distal sensing electrode 720 may have a tapered shape at the distal end 726 of the lead 702 to carve through the tissue. For example, the electrode 720 may have a bullet-like shape as shown in the side view of FIG. 7B. The tapered shape enables blunt dissection with less input force and less damage to the tissue than if the distal end 726 has a shape that is more blunt. The lead 702 itself may represent a tunneling tool that creates the channel, obviating the need to create a channel prior to lead insertion. In another example self-implanting application, a discrete tunneling tool may be used first to form the channel through the patient tissue, and then the tunneling tool may be extracted before the lead 702 is inserted into the channel using the implant tool 802.

Furthermore, to increase the rigidity of the lead 702 for the blunt dissection, the implant tool 802 is designed to be inserted through the lumen 804. The implant tool 802 has a handle 812 and a rod 814 or pole that extends from the handle 812 to a distal end 816 of the rod 814. The rod 814 is linear and is sized to fit within the lumen 804. The implant tool 802 may be rigid. For example, the implant tool 802 may include one or more metals. In an embodiment, to implant the lead 702, the rod 814 of the implant tool 802 is inserted into the lumen 804 through the inlet 806 in the boot 728. The rod 814 traverses through all or at least most of the brick segments 710. With the rod 814 extending through the brick segments 710 the primary electrode 704 is relatively rigid, such that the amount that the brick segments 710 are permitted to pivot relative to one another is substantially limited and the primary electrode is substantially linear. During the implant procedure, the operator uses the handle 812 to manipulate the lead 702 into a desired implant position within the channel of the patient. Once in place, the operator extracts the implant tool 802 from the lead 702 by pulling the tool 802 such that the rod 814 exits the lumen 804. The lead 702 is left in place, and the incision in the patient is closed.

In an embodiment, a distal tip 818 of the rod 814 may include a securing feature 820 for removably coupling to the distal sensing electrode 720 and/or the distal-most brick segment 710. For example, the securing feature 820 may include helical threads that can couple to complementary threads 822 near the end 808 of the lumen 804. The coupling between the rod 814 and the lead 702 can be useful, particularly for extracting the lead 702 from the patient if necessary.

Referring now back to FIGS. 7A and 7D with continued reference to FIG. 8, the lead 702 may include flushing holes 750 that are fluidly connected to the lumen 804. The flushing holes 750 may emit a flushing fluid, such as a saline solution, into the internal cavity of the patient to wet the outer surfaces of the lead 702. In the illustrated embodiment, the brick segments 710 define the flushing holes 750. The flushing holes 750 connect to the cavities 736 of the brick segments 710. In an embodiment, the internal cavity of the patient may be flushed by injecting the flushing fluid into the lumen 804 through the inlet 806, such as via a syringe. The fluid is emitted or secreted from the lead 702 at different locations along the length of the lead 702 via the flushing holes 750. Some of the fluid may be emitted at the joints 712 between the brick segments 710. Ejecting the fluid at different locations and directions from the lead 702 may provide more reliable, effective, and/or cleaner establishment of the fluid-electrode interface without air bubbles. It is noted that the lead 702 itself in this embodiment functions similar to the sheath 304 described in FIGS. 3 and 4, such that a discrete flushing sheath is not needed. In an alternative embodiment, the lead 702 does not include the flushing holes 750 because the joints 712 may function as flushing holes. For example, a sufficient amount of saline solution or other fluid injected into the lumen 804 may be emitted from the lead 702 at different locations along the length via the joints 712, so discrete flushing holes 750 are unnecessary.

In an alternative embodiment, the lead 702 is not self-implantable via blunt dissection. For example, the lead 702 does not include the lumen 804, and the brick segments 710 of the primary shocking electrode 704 do not include the cavities 736. In this alternative embodiment, the lead 702 with the segmented primary shocking electrode 704 may be implanted via the implant tool assembly 300 shown in FIGS. 3 and 4, or a similar tool assembly.

In the illustrated embodiment, the primary shocking electrode 704 is segmented into brick segments 710, and the secondary shocking electrode 706 is not segmented. In another embodiment, the secondary shocking electrode 706 is segmented into brick segments and has a similar construction as the primary shocking electrode 704. Optionally, the secondary shocking electrode 706 may be shorter in length than the primary shocking electrode 704, such as with fewer brick segments or smaller brick segments than the primary electrode 704.

Figure 9:
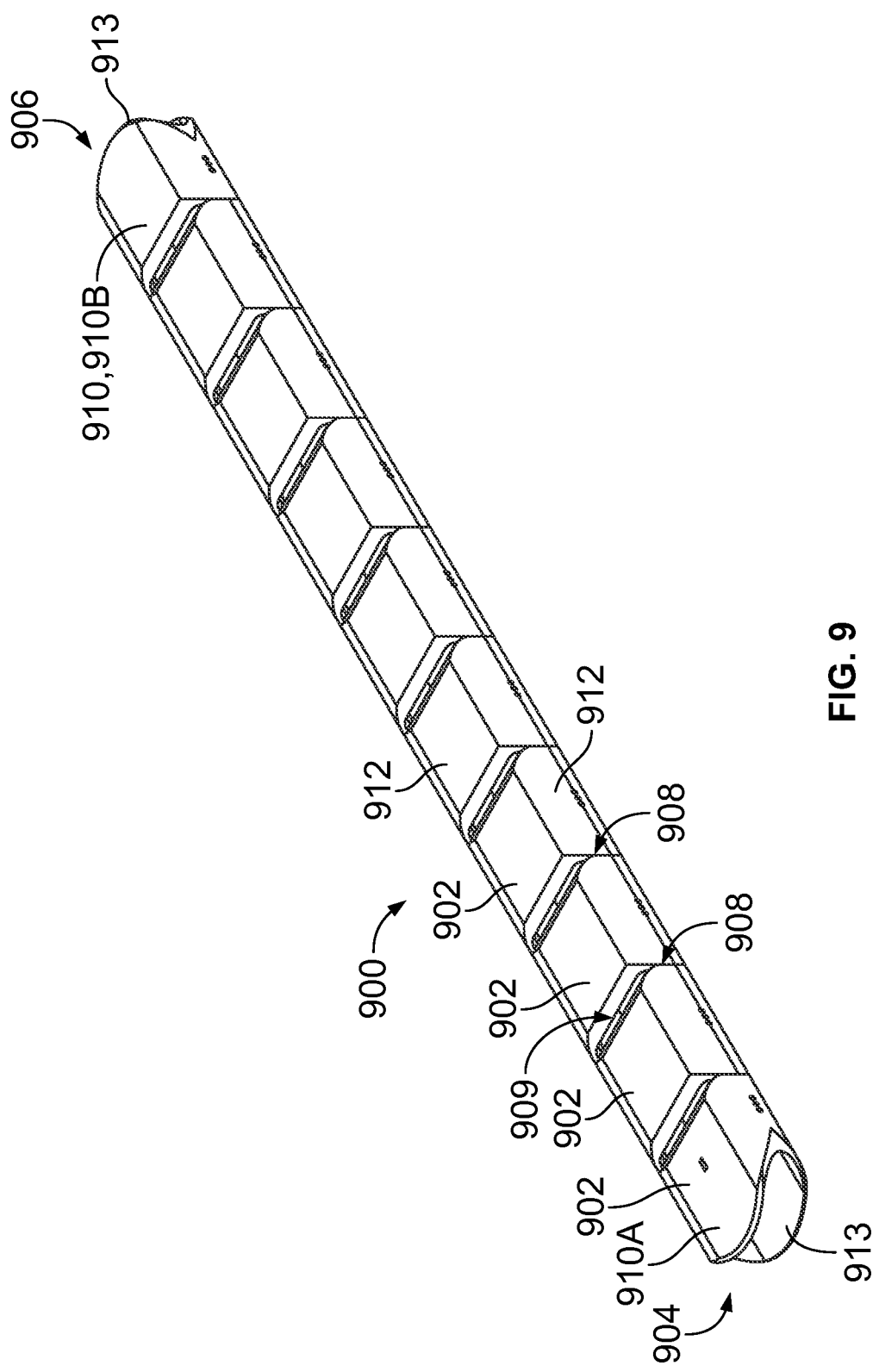
FIG. 9 is a perspective view of an electrode for a lead of an IMD according to an embodiment.

FIG. 9 is a perspective view of an electrode 900 for a lead of an IMD according to an embodiment. The electrode 900 may be designed for a subcutaneous lead of a S-ICD. The electrode 900 may be a shocking electrode that is powered by a pulse generator of an IMD to deliver high-voltage shocks for defibrillation treatment. The electrode 900 shown in FIG. 9 may be a variation (e.g., alternative embodiment) of the modular primary shocking electrode 704 shown in FIG. 7A. The electrode 900 could replace the primary shocking electrode 704, the secondary shocking electrode 706, or both the primary and secondary shocking electrodes 704, 706 of the lead 702 in FIG. 7A.

The electrode 900 is modular, such that the electrode 900 is formed by a plurality of discrete brick segments 902 assembled together. The brick segments 902 are mechanically connected to one another in a line, similar to the brick segments 710 in FIG. 7A. For example, the electrode 900 may have a proximal end 904 and a distal end 906 opposite the proximal end 904. The line brick segments 902 may define a single-file line that extends from the proximal end 904 to the distal end 906. The brick segments 902 may define the proximal and distal ends 904, 906. The length of the electrode 900 is the distance along the electrode 900 between the proximal and distal ends 904, 906. The length is determined by the respective lengths and the number of the brick segments 902 in the line. There are ten brick segments 902 in the illustrated embodiment. A benefit of the modular electrode 900 is that the length of the electrode 900 can be customized for a patient by selecting the number of brick segments 902 to include in the line. For example, a tall adult may receive an implantable lead with an electrode that has more brick segments, and therefore a longer length, than the electrode on the lead implanted in a juvenile or short adult. Adjacent brick segments 902 are mechanically connected to each other at joints 908. The electrode 900 may include seams at the joints 908. Optionally, the brick segments 902 may define depressions 909 at the joints 908, at least along one side of the electrode 900. The depressions 909 may promote tissue in-growth to reduce the risk of lead/electrode migration from the implanted location over time.

FIG. 9 is an isolated view of the electrode 900 without depicting the lead body of the lead or any other components, such as sensing electrodes, fixation elements for securing the lead in place, or the like. The lead body may extend from the electrode 900 to the pulse generator of the IMD. The lead body may be the lead body 724 in FIG. 7A and/or the lead body 121 in FIG. 1. The pulse generator may be the pulse generator 22 in FIG. 6 and/or the pulse generator 105 in FIG. 1. When the lead is assembled, the lead body, a sensing electrode, a fixation element, and/or the like may couple to and extend from the proximal end 904 of the electrode 900. Similarly, the lead body, a sensing electrode, a fixation element, and/or the like may couple to and extend from the distal end 906.

The brick segments 902 are electrically conductive, and are electrically connected to one another across the joints 908. For example, the brick segments 902 may be electrically commoned to one another. The electrode 900 may receive power (e.g., electric current) from the pulse generator via the lead body. The received power may be emitted from the brick segments 902 of the electrode 900 as high-voltage shocks for defibrillation therapy. In order to convey the power from the pulse generator to the electrode 900, at least one electrical wire of the lead body may be welded, crimped, or otherwise secured to at least one of the brick segments 902 to establish an electrically conductive pathway extending from the pulse generator to the electrode 900.

The brick segments 902 may be composed of one or more electrically conductive materials that are safe for human tissue interaction. In an embodiment, the brick segments 902 include one or more metals, such as titanium, nickel, chromium, cobalt, stainless steel, and/or the like. In an example, the brick segments 902 may be stamped and formed from a thin panel of sheet metal. Forming from sheet metal may enable the brick segments 902 to be relatively lightweight and hollow, utilizing a limited amount of metal material. In another example, the brick segments 902 may be formed by a different process, such as machining, molding (e.g., casting), or the like.

In an embodiment, the brick segments 902 include end pieces 910 and middle pieces 912. The middle pieces 912 can mechanically couple to each other and to the end pieces 910. In an example, a first end piece 910A defines the proximal end 904 and a second end piece 910B defines the distal end 906. The middle pieces 912 are disposed between the end pieces 910A, 910B along the line of the electrode 900. The middle pieces 912 may be copies or replicas of each other, such that the middle pieces 912 all have the same size, shape, and dimensions (e.g., within manufacturing tolerances). The electrode 900 may have any number of middle pieces 912 depending on a desired length of the electrode 900. In an example, the end pieces 910A, 910B and the middle pieces 912 all have oblong cross-sectional shapes, which are shown in more detail in FIG. 10. For example, the cross-sectional shapes defined by the outer perimeters of the brick segments 902 may be a racetrack, rectangle with curved corners, elliptical, oval, or the like. In an example, the end pieces 910A, 9106 have a different shape than the middle pieces 912. For example, the end pieces 910A, 910B may include convex mouths 913 at the proximal and distal ends 904, 906, respectively, which are not present on the middle pieces 912. The convex mouths 913 may provide a smooth transition to an adjacent portion of the lead that has a reduced cross-sectional size (e.g., diameter) relative to the electrode 900, as well as limit snagging against patient tissue along the transition region. The end pieces 910A, 9106 are arranged such that the convex mouths 913 face outward away from each other. In an alternative embodiment, the electrode 900 may lack the end pieces 910, and may be formed entirely of brick segments 902 in the form of the middle pieces 912.

Figure 10:
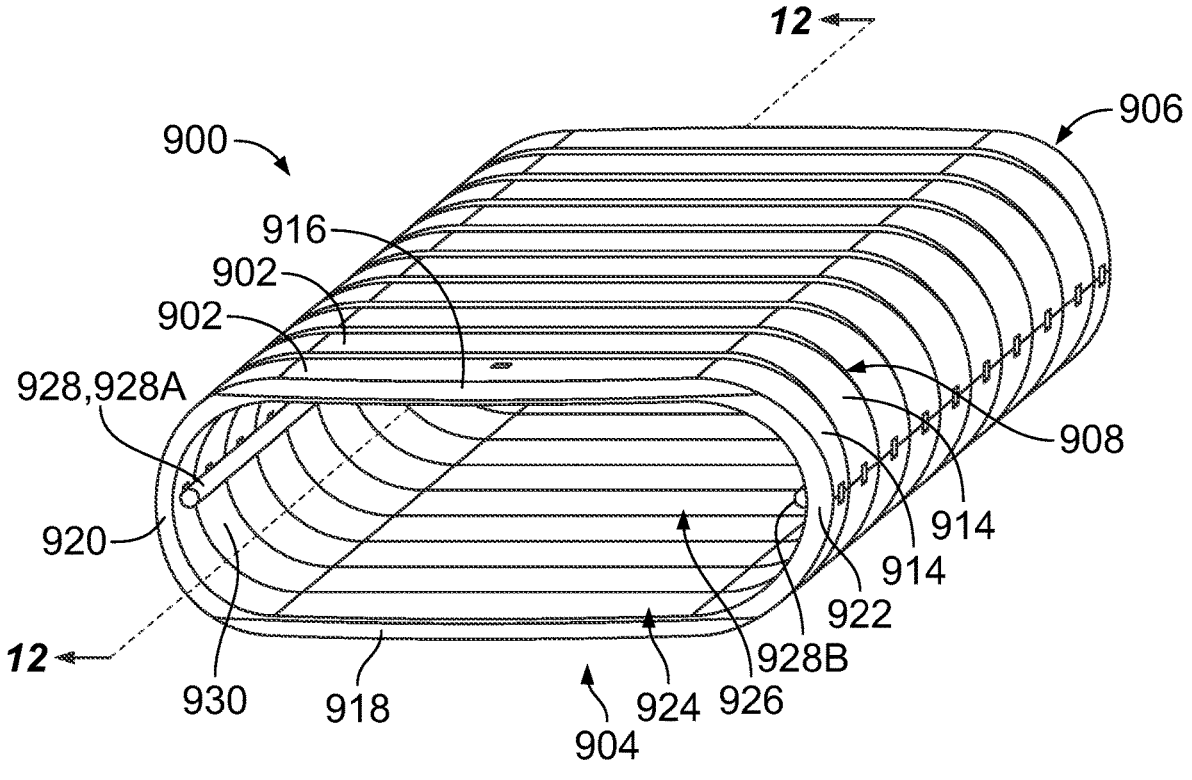
FIG. 10 is an elevational view showing an end of the electrode of FIG. 9.

FIG. 10 is an elevational view showing an end of the electrode 900 of FIG. 9. The end in the forefront of FIG. 10 may be the proximal end 904. Each brick segment 902 includes a body 914 that defines the cross-sectional shape of the brick segment 902. In the illustrated embodiment, the cross-sectional shape of the brick segments 902 is a race-track. For example, an upper portion 916 and a lower portion 918 of the body 914 are linear or flat, and a first lateral portion 920 and a second lateral portion 922 of the body 914 are curved from the upper portion 916 to the lower portion 918. The body 914 may define a hollow cavity 924 through the body 914. When the brick segments 902 are assembled into the electrode 900, the individual hollow cavities 924 align to form a central channel 926 (e.g., lumen) of the electrode 900.

In the illustrated embodiment, each brick segment 902 defines a single, large hollow cavity 924. The bodies 914 are relatively thin, and the hollow cavities 924 represent a majority of the cross-sectional area of the brick segments 902. As described above, the bodies 914 optionally may be stamped and formed from sheet metal. The relatively large central channel 926 through the electrode 900 could accommodate the lead body of the lead. For example, the lead may be assembled by inserting the lead body at least partially through the central channel 926 of the electrode 900. Optionally, the lead body may fully extend through the central channel 926 and protrude from both ends 904, 906. The relatively large central channel 926 may also permit flushing the electrode 900 during the implant procedure to avoid air bubbles. For example, fluid may be introduced into the central channel 926 at the proximal end 904 and may exit the central channel 926 through the joints 908 and/or the distal end 906.

In an embodiment, the brick segments 902 are mechanically connected to each other in the line via the use of one or more support cables 928. The electrode 900 includes two support cables 928 in the illustrated embodiment. The support cables 928 both extend along multiple brick segments 902, and may extend along all of the brick segments 902 in the line. One support cable 928A is disposed along the first lateral portions 920 of the brick segments 902. The other support cable 928B is disposed along the second lateral portions 922 of the brick segments 902, such that the cables 928A, 928B are located along opposite lateral sides of the electrode 900. The electrode 900 may include a different number of support cables 928 and/or different placement of the support cables 928 in other embodiments. The support cables 928 are affixed to at least some of the brick segments 902 to secure the brick segments 902 to one another in the line. For example, the support cables 928 exert tension to avoid the brick segments 902 separating and moving apart at the joints 908. Optionally, the support cables 928 may be affixed to each of the brick segments 902. Alternatively, the support cables 928 may be affixed to a subset, but not all, of the brick segments 902, and tension provided by the brick segments 902 that are attached to the support cables 928 may hold non-affixed brick segments 902 located therebetween in place. The support cables 928 may be affixed to the brick segments 902 via welding, crimping, bonding, or the like.

Figures 11, 12:
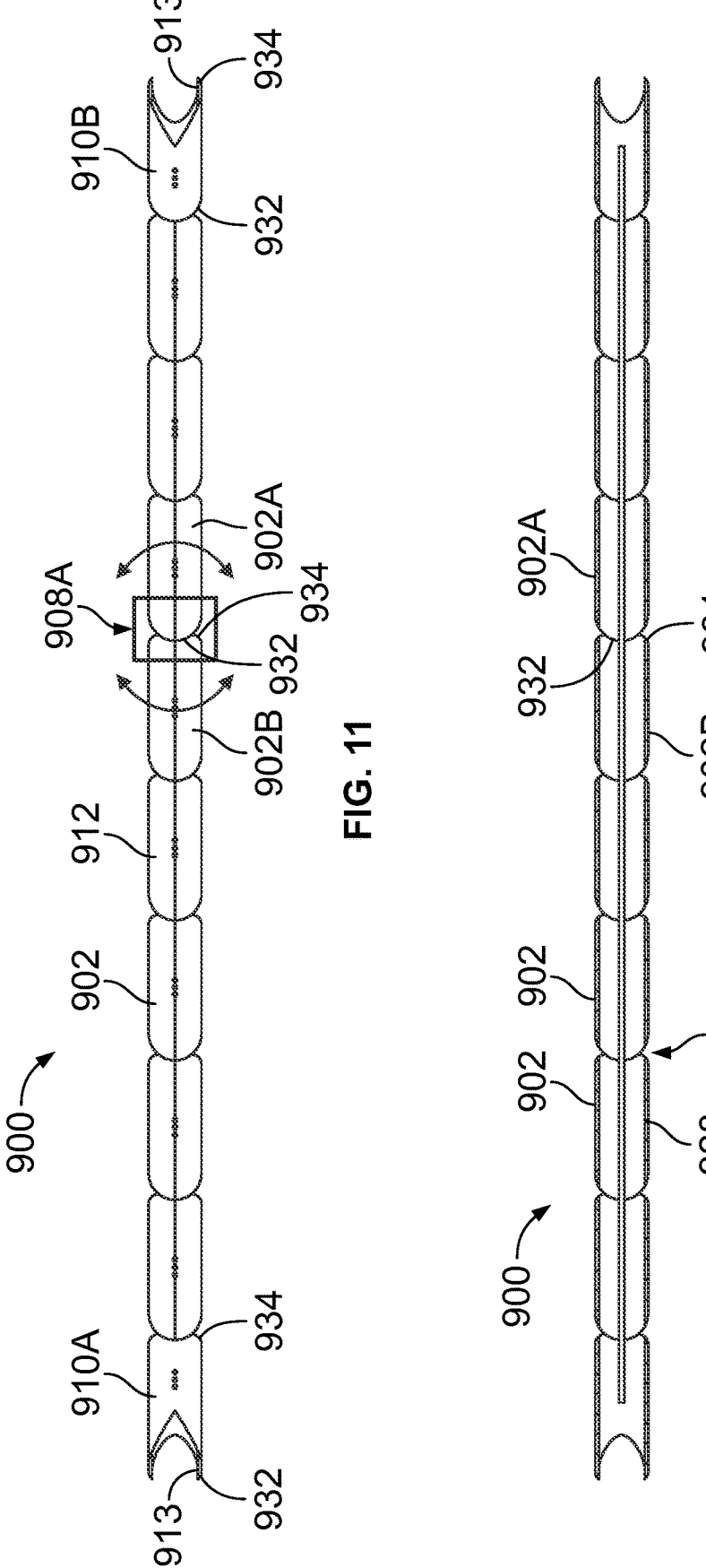
FIG. 11 is a side view of the electrode shown in FIGS. 9 and 10.
FIG. 12 is a side cross-sectional view of the electrode shown in FIGS. 9 through 11.

The tension of the support cables 928 may be selected or adjusted to enable some flexibility of the electrode 900 along the joints 908 between the brick segments 902. For example, as shown in FIG. 11, the brick segments 902 may be pivotable relative to each other in at least one dimension (e.g., one degree of freedom). In an example, the electrode 900 can flex in the vertical (e.g., up and down) dimension at the joints 908. For example, the upper portion 916 of some brick segments 902 may be disposed at a different vertical position (e.g., height) relative to the upper portion 916 of other brick segments 902, causing the electrode 900 to have a bowed and/or undulating shape in the vertical dimension along its length. Optionally, the electrode 900 may also flex in at least one other dimension, such as the lateral (e.g., side-to-side) dimension. The tension of the support cables 928 may be sufficiently relaxed to enable at least slight flexibility of the electrode 900 at the joints 908 in the lateral dimension. The flexible characteristic of the electrode 900 may beneficially allow the electrode 900 to follow a contour of the patient's body structure upon implant, such as along the contour of the sternum. Furthermore, the flexible electrode 900 may adapt to the contour of the patient's body even as the patient moves within a normal range of movement, to avoid causing pain or discomfort, and to avoid excessive protrusion underneath the skin that could contribute to body dysmorphia issues.

The support cables 928 may be formed of any material that provides sufficient strength to structurally support the electrode 900. In an embodiment, the support cables 928 are electrically conductive. In addition to providing mechanical support and retention, the electrically conductive support cables 928 may provide electrically conductive pathways between the brick segments 902 to electrically connect the brick segments 902. For example, the support cables 928 may be formed of a metal material, such as stainless steel. The support cables 928 may be the same as the cables 718 shown in FIG. 7A. In an example, the support cables 928 may be welded to the brick segments 902 and may provide reliable electrically conductive pathways between the brick segments 902.

Figure 14:
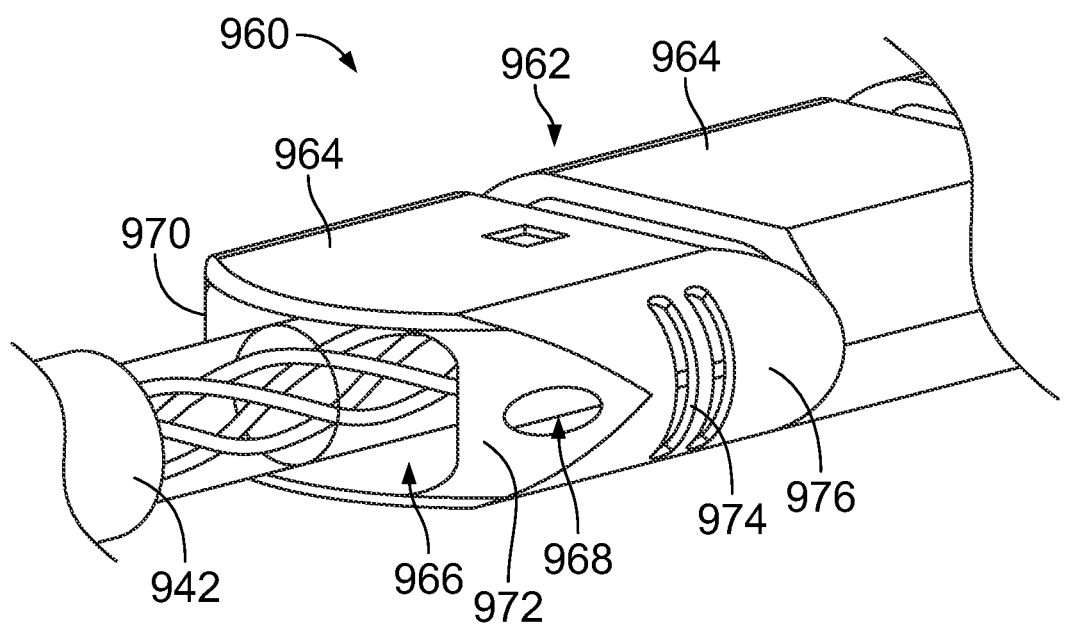
FIG. 14 illustrates a perspective view of a portion of a lead that includes an electrode according to another embodiment.

In the illustrated embodiment, the support cables 928A, 928B are disposed within the central channel 926 of the electrode 900 and are affixed to respective interior surfaces 930 of the bodies 914 of the brick segments 902. The interior surfaces 930 define the hollow cavities 924 of the individual brick segments 902. Optionally, the support cables 928A, 928B may be welded to the interior surfaces 930 of the bodies 914. In an alternative embodiment, the support cables 928 may extend through the bodies 914 of the brick segments 902 without being within the hollow cavities 924, as shown in FIG. 14 for example. In another alternative embodiment, the support cables 928 may be disposed along an outer (e.g., exterior) perimeter of the brick segments 902. For example, the bodies 914 may define grooves along the outer perimeter, and the support cables 928 may be received into the grooves such that the support cables 928 are either flush with, or recessed below, the outer perimeter of the electrode 900.

FIG. 11 is a side view of the electrode 900 shown in FIG. 9 and FIG. 12 is a side cross-sectional view of the electrode 900 shown in FIGS. 9 through 11. The cross-section is taken along line 12-12 in FIG. 10. FIG. 12 shows one of the support cables 928 continuously extending along all of the brick segments 902 in the line, such that the support cable 928 extends across all of the joints 908. With reference to both FIGS. 11 and 12, adjacent brick segments 902 may nest together at the corresponding joint 908 defined between the adjacent brick segments 902. Two brick segments are considered adjacent when there is no other brick segment disposed between the two brick segments in the line. In an example, each brick segment 902 may longitudinally extend from a first end 932 of the brick segment 902 to a second end 934 of the brick segment 902 opposite the first end 932. At a given joint 908, the first end 932 of one brick segment 902 nests within the second end 934 of an adjacent brick segment 902 in the line. At the joint 908A highlighted in FIG. 11, the first end 932 of a first brick segment 902A nests within the second end 934 of a second brick segment 902B. For example, the first ends 932 may be at least partially received into openings at the second ends 934 of the adjacent brick segments 902, such that the first ends 932 at least partially overlap the second ends 934. The first ends 932 may have a convex curve that tapers to enable the first end 932 to be partially received into the adjacent brick segment 902. Optionally, the second ends 934 may have a concave curve that accommodates the convex curve of the first ends 932. Thus, the first end 932 of each middle piece 912 may be a plug or nesting end, and the second end 934 of each middle piece 912 may be a socket or receiving end that is designed to accommodate the plug or nesting end of an adjacent brick segment.

In an embodiment, the brick segments 902 are pivotable at the nested joints 908. For example, the first brick segment 902A may be pivotable relative to the second brick segment 902B, and vice-versa, at the joint 908A as indicated by the arrows. The brick segments 902 may pivot in the vertical (e.g., height) dimension at the joints 908, which is up and down in the illustrated orientation shown in FIGS. 11 and 12. Optionally, as described above, the brick segments 902 may be permitted at least slight movement relative to one another in the lateral dimension, which is in and out of the page in the illustrated orientation shown in FIGS. 11 and 12. The brick segments 902 may nest at the joints 908 while retaining the large central channel 926 shown in FIG. 10.

In the illustrated embodiment, the first and second end pieces 910A, 910B may be different from one another due to the nesting arrangement. For example, the first end 932 of the first end piece 910A is the convex mouth 913, and the second end 934 defines the socket or receiving end. The first end 932 of the second end piece 9106 is the plug or nesting end, and the second end 934 of the second end piece 910B is the convex mouth 913.

Figure 13:
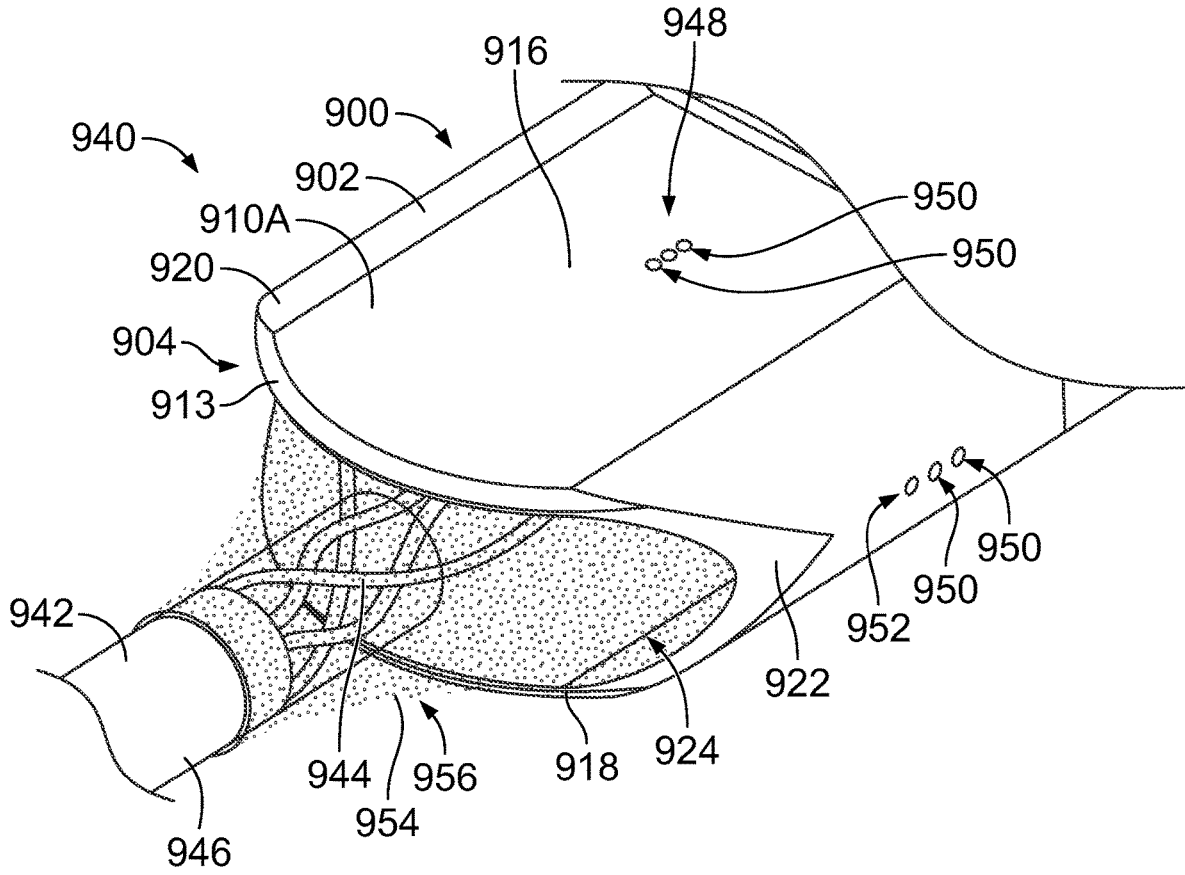
FIG. 13 illustrates a perspective view of a portion of a lead that includes the electrode shown in FIGS. 9 through 12 according to an embodiment.

FIG. 13 illustrates a perspective view of a portion of the lead 940 that includes the electrode 900 according to an embodiment. FIG. 13 only shows a section of the electrode 900 including the proximal end 904. The section includes the first end piece 910A of the brick segments 902. The lead 940 includes a lead body 942 that mechanically and electrically connects to the electrode 900. The lead body 942 may be a cable that includes one or more electrical wires 944 within an outer sheath or jacket 946. In the illustrated embodiment, the lead body 942 has multiple electrical wires 944. The electrical wires 944 may be co-wound. The lead body 942 may extend from the electrode 900 to the pulse generator of the IMD. The lead body 942 may be mechanically and electrically connected to the pulse generator in order to convey electrical power (e.g., electric current) from the pulse generator to the electrode 900 to deliver high-voltage shocks for defibrillation therapy. The electrical power is conveyed along at least one of the electrical wires 944 of the lead body 942, which is electrically connected to at least one of the brick segments 902 of the electrode 900.

In an embodiment, the electrical wire (or wires) 944 that powers the electrode 900 is welded to the first end piece 910A brick segment 902. Optionally, the first end piece 910A defines a first set 948 of one or more weld holes or slots 950 fully extending through a thickness of the body 914 of the first end piece 910A. The weld holes or slots 950 are designed to permit welding the electrical wire 944 to the interior surface 930 (shown in FIG. 10) of the first end piece 910A. The first set 948 is disposed in the upper portion 916 in FIG. 13, but may be located in the lower portion 918 or one of the lateral portions 920, 922 in another embodiment. For example, laser welding may be performed through the weld holes or slots 950 from a weld tool located outside of the hollow cavity 924, which may simplify the welding process relative to attempting to position the weld tool within the hollow cavity 924.

In an embodiment, the first end piece 910A also includes at least a second set 952 of one or more weld holes or slots 950 fully extending through the thickness of the body 914. The second set 952 is disposed along the second lateral portion 922. The second set 952 may permit welding one of the support cables 928B (shown in FIG. 10) to the first end piece 910A to affix the support cable 928B to the first end piece 910. The first end piece 910A may also include a third set (not shown) of one or more weld holes or slots 950 defined through the body 914 at the first lateral portion 920 to permit welding the other support cable 928A (shown in FIG. 10) to the first end piece 910A.

In an example, an insulative material 954 can be installed between the lead body and the electrode 900 along a transition section 956 of the lead 940. The insulative material 954 may provide a smooth transition from the smaller size of the lead body 942 to the larger size of the brick segment 902. The insulative material 954 may be molded or reflowed in-situ to conform around the lead body 942 and substantially fill the hollow cavity 924 at the convex mouth 913. The insulative material 954 may support mechanical coupling of the lead body 942 to the electrode 900. For example, the insulative material 954 may be applied in a fluid state, such that the insulative material 954 flows around and within the contours of the lead body 942 and the first end piece 910A to conform to the contours. Upon solidifying, the insulative material 954 may grip both the lead body 942 and the first end piece 910A to secure the lead body 942 to the first end piece 910A, as well as optionally also seal the hollow cavity 924 and provide electrical insulation. In an example, the insulative material 954 may include silicone rubber, polyurethane, and/or the like.

FIG. 14 illustrates a perspective view of a portion of a lead 960 that includes an electrode 962 according to an embodiment. The electrode 962 may be a variation (e.g., alternative embodiment) of the electrode 900 shown in FIGS. 9 through 13. For example, the electrode 962 may be modular and defined by multiple brick segments 964 that are similar to the brick segments 902. Furthermore, the brick segments 964 may be tied together in a line via the use of one or more support cables (not shown) similar to the support cables 928. The electrode 962 may differ from the electrode 900 in the placement of the support cables. For example, the brick segments 964 define respective hollow cavities 966 and also define apertures 968 that are discrete from the hollow cavities 966. The lead body 942 is received within the hollow cavity 966, as described above with reference to FIG. 13. The support cables are received and held within the apertures 968. The brick segment 964 shown at the end of the line has first and second lateral portions 970, 972, and the hollow cavity 966 is disposed between the first and second lateral portions 970, 972.

Each of the first and second lateral portions 970, 972 may define a respective aperture 968, although only one of the apertures 968 is visible in FIG. 14. The apertures 968 may extend the length of the respective brick segment 964. When assembled in the line, the apertures 968 of adjacent brick segments 964 align. The support cables may be installed within the apertures 968 to extend along the brick segments 964. The support cables within the apertures 968 may be affixed to the brick segments 964 via welding, crimping, bonding, or the like. In the illustrated embodiment, the brick segment 964 includes crimp ribs 974 along which the brick segment 964 is crimped onto the support cable within the corresponding aperture 968 to mechanically lock the brick segment 964 to the support cable.

In another embodiment, a similar functional effect may be accomplished by defining grooves (e.g., depressions, recesses, indentations, etc.) in the outer surface 976 of the brick segments 964 at the first and second lateral portions 970, 972. The grooves may replace the apertures 968. For example, the grooves along one side may be sized to accommodate the support cable such that the support cable within the grooves are either flush with, or recessed within, the plane of the outer surface 976. The support cable may be affixed to the brick segments 964 within the grooves via welding, crimping, bonding, or the like. For example, crimping may be performed by pinching a portion of the brick segment 964 that surrounds the groove onto the support cable within the groove to lock the support cable to the brick segment 964.

Figure 15:
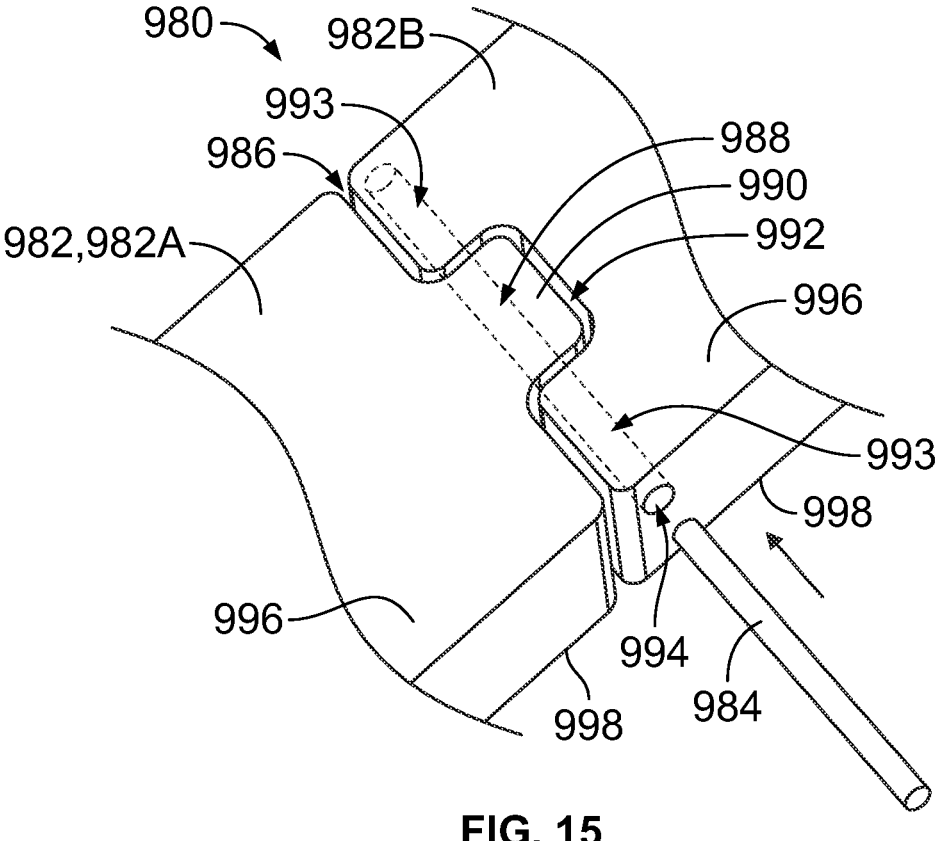
FIG. 15 illustrates a portion of a modular electrode according to another embodiment.

FIG. 15 illustrates a portion of a modular electrode 980 according to another embodiment. The electrode 980 may be a variation (e.g., alternative embodiment) of the electrode 900 shown in FIGS. 9 through 13 and the electrode 962 shown in FIG. 14. The electrode 980 is defined by multiple brick segments 982 that are similar to the brick segments 902, 964 in that the brick segments 982 may be electrically conductive to deliver shocks for defibrillation therapy, may be arranged in a line, and may define a central channel to accommodate a lead body. The electrode 980 differs from the electrodes 900 and 962 in the coupling mechanism between the adjacent brick segments 982. For example, the electrode 980 does not include support cables that extend the length of the electrode 980. The electrode 980 includes pins 984 at the joints 986 between adjacent brick segments 982. The pins 984 extend through pinholes defined in each brick segment 982 at a joint 986 and mechanically connect the adjacent brick segments 982 together.

In the illustrated embodiment, the brick segments 982 have a puzzle-like mating interface in which a first brick segment 982A includes a protrusion 990 and the adjacent second brick segment 982B includes a cutout or recess 992 that receives the protrusion 990 therein when the brick segments 982A, 982B are aligned and proximate to each other. The protrusion 990 defines a first pinhole 988 (shown in phantom) that aligns with second pinholes 993 defined through the second brick segment 982B. The pin 984 is loaded into an opening 994 to continuously extend through both the first and second pinholes 988, 993, which secures the brick segments 982A, 982B together at the joint 986. For example, the pin 984, when installed, may be laterally oriented, perpendicular to the length of the electrode 980. In an example, the pinholes 988, 993 may be defined through one of the wide portions of the brick segments 982, such as the upper portion 996 or the lower portion 998, to avoid interfering with the central channel that is defined through the electrode 980. In an alternative embodiment, the pin may be an integral component of one of the brick segments 982 rather than a discrete element. For example, the protrusion 990 may include two nubs or posts extending in opposite lateral directions from the protrusion 990. The nubs or posts may be received into corresponding detents or depressions along side surfaces of the recess 992 to secure the two brick segments 982 together at the joint.

The modular electrodes shown in FIGS. 7A-7D and FIGS. 8 through 15 can be made at variable lengths to create longer/shorter shocking electrodes as needed while still having increased flexibility compared to a solid piece of metal. The added surface area of the oblong electrodes help decrease shocking impedance, which in turn reduces the required device capacitance requirements. The reduced device capacitance requirements may permit reducing the size of the pulse generator device and/or the lead body. The small gaps between the brick segments, where mated together, may allow for a tissue ingrowth over a chronic implantation period, which helps to prevent migration of the lead body/shocking electrode over time.

FIG. 16 is a flow chart 1000 of a method for producing a lead for an implantable medical device (IMD) according to an embodiment. The lead that is produced according to the method in FIG. 16 may be any of the leads having modular electrodes as described with reference to FIGS. 7A-7D and 8 through 15. The method may include additional steps than shown in FIG. 16, fewer steps than shown in FIG. 16, and/or different steps than shown in FIG. 16.

At step 1002, an electrode is formed by mechanically connecting a plurality of brick segments to one another in a line. The brick segments may be discrete objects. The brick segments may be electrically conductive and electrically connected to one another in the line. The brick segments may be powered by a pulse generator of the IMD to deliver high-voltage shocks for defibrillation therapy. Each of the brick segments may have an oblong cross-sectional shape. Optionally, each brick segment longitudinally extends from a first end of the brick segment to a second end of the brick segment opposite the first end. Forming the electrode may include nesting the first end of a first brick segment within the second end of a second brick segment that is adjacent to the first brick segment along the line to form a joint.

At step 1004, the electrode is formed by affixing one or more support cables, that extend along the brick segments, to the brick segments to secure the brick segments one another in the line. The one or more support cables may be affixed to the brick segments by welding the one or more support cables to the brick segments. Alternatively, or in addition, the one or more support cables may be affixed to the brick segments by crimping the brick segments onto the one or more support cables.

At step 1006, the electrode is formed by installing pins into the brick segments at the joints, rather than affixing one or more support cables to the brick segments at in step 1004.

At step 1008, a lead body is secured to the electrode and electrically connected to the electrode. The lead body may convey power from the pulse generator to the electrode for the defibrillation therapy.

At step 1010, the lead is implanted such that the electrode is disposed in a subcutaneous location within the patient.

Figures 17A, 17B, 17C:
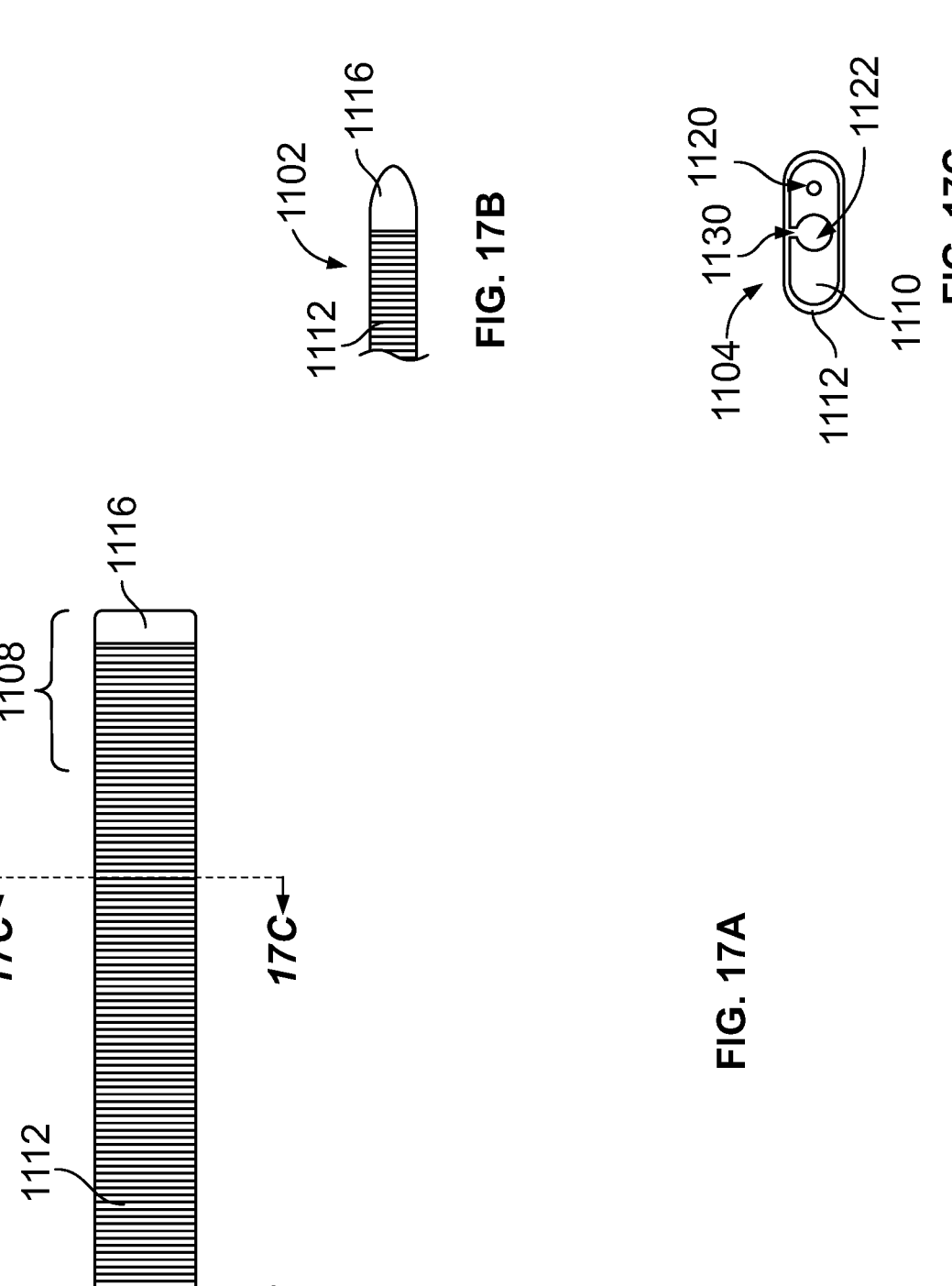
FIG. 17A illustrates a plan view of a lead according to an embodiment.
FIG. 17B is a side view of a distal portion of the lead shown in FIG. 17A.
FIG. 17C illustrates a cross-sectional shape of a primary shocking electrode taken along line 17C-17C in FIG. 17A.

FIG. 17A illustrates a plan view of a lead 1102 according to an embodiment. The lead 1102 may be the lead 120 shown in FIG. 1. The lead 1102 includes a primary shocking electrode 1104 and a secondary shocking electrode 1106. FIG. 17B is a side view of a distal portion 1108 of the lead 1102 shown in FIG. 17A. FIG. 17C illustrates a cross-sectional shape of the primary electrode 1104 taken along line 17C-17C in FIG. 17A. The primary shocking electrode 1104 and the secondary shocking electrode 1106 optionally may represent the primary shocking electrode 126 and the secondary shocking electrode 128, respectively. For example, the primary electrode 1104 may have an oblong cross-sectional shape, as shown in FIG. 17C.

The primary electrode 1104 of the lead 1102 in FIGS. 17A-C is not segmented into multiple electrically conductive brick segments. Rather, the primary electrode 1104 includes an electrically insulative (e.g., dielectric) base 1110 and a coiled wire 1112 that surrounds the base 1110. The base 1110 may be composed of silicone rubber, polyurethane, and/or the like. The base 1110 may be sufficiently flexible to enable the primary shocking electrode 1104 to confirm to the contour of the patient's body. Optionally, the base 1110 may have the same or similar compositions as a lead body 1114 of the lead 1102. The coiled wire 1112 may be an electrically conductive metal that is wound and/or wrapped around the base 1110, between a distal sensing electrode 1116 and a proximal sensing electrode 1118. The sensing electrodes 1116, 1118 optionally may be the same as the electrodes 720, 722 shown in FIGS. 7A, 7B, and 8. In an embodiment, the base 1110 is unitary and extends the entire length of the primary electrode 1104 between the sensing electrodes 1116, 1118. In an alternative embodiment, the electrically insulative base 1110 may be segmented into multiple discrete brick segments. The brick segments may be similar in shape as the brick segments 710, although different in material composition. The brick segments may be coupled together via one or more wires or cables, as described above.

In an embodiment, the base 1110 defines one or more wire openings 1120 for receiving electrical wire(s) therethrough. The base 1110 may define a lumen 1122 for receiving flushing fluid and/or the rod 814 of the implant tool 802 shown in FIG. 8. For example, the lead 1102 may be self-implantable via blunt dissection. The implant tool 802 may be used to implant the lead 1102 in the same or a similar fashion as the implantation of the lead 702 described above with reference to FIG. 8. Optionally, the base 1110 defines a plurality of flushing holes 1130 for emitting flushing fluid, such as a saline solution. One flushing hole 1130 is shown in FIG. 17C. The flushing holes 1130 are fluidly connected to the lumen 1122. The flushing holes 1130 may be used to wet the interface between the base 1110 and the coiled wire 1112 and/or wet the lead-tissue interface.

FIG. 18 is a flow chart 1200 of a method for implanting a subcutaneous lead of an IMD according to an embodiment. The method may include additional steps than shown in FIG. 18, fewer steps than shown in FIG. 18, and/or different steps than shown in FIG. 18. The method may be performed with one of the leads 702, 940, 960, 1102 shown in FIGS. 7A, 13, 14, and 17A, respectively. At step 1202, a rod 814 of an implant tool 802 is inserted into a lumen or central channel of a lead. The lumen or central channel extends through a primary shocking electrode 704, 900, 962, 980, 1104 of the lead.

At step 1204, the lead is implanted into an internal cavity in a patient through an incision by manipulating the implant tool 802. The lead is designed with a tapered distal end to perform blunt dissection of patient tissue during the implant process. An operator, such as a human or a robot, may grasp a handle 812 of the implant tool 802 to load the lead, with the rod 814 therein, into the patient internal cavity.

At step 1206, the implant tool 802 is extracted from the internal cavity of the patient without the lead, such that the lead remains implanted. For example, the rod 814 may be pulled out from the lumen via the handle 812. In an embodiment, the steps described above are used to implant a distal segment of the lead, such as along a parasternal area of the patient. The same steps may be repeated to implant a proximal segment of the lead, which includes a secondary electrode. For example, the rod 814 of the implant tool 802 may be inserted into a lumen of the secondary electrode to insert the proximal segment into the patient. The proximal segment may be a transverse portion of the lead.

At step 1208, the lead and patient internal cavity may be flushed with a fluid, such as saline, by injecting the fluid into the lumen. The fluid may be ejected at different locations along the length of the shocking electrode through flushing holes 750, 1130 and/or through joints between brick segments of the electrode. The proximal segment of the lead may be flushed as well.

At step 1210, a proximal end of the lead may be mechanically coupled and electrically connected to a pulse generator 105 to render the IMD operable.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage media having computer (device) readable program code embodied thereon.

Any combination of at least one non-signal computer (device) readable medium may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A lead for an implantable medical device (IMD) comprising:
an electrode comprising a plurality of brick segments that are discrete and mechanically connected to one another in a line, wherein the brick segments are electrically conductive and electrically connected to one another, wherein a distal end of a first brick segment of the electrode is connected to a proximal end of a second brick segment of the electrode at a first joint, and a proximal end of the first brick segment is connected to a distal end of a third brick segment of the electrode at a second joint, the brick segments configured to be powered by a pulse generator of the IMD to deliver high-voltage shocks for defibrillation therapy; and wherein the distal end of the first brick segment is connected to the proximal end of the second brick segment at the first joint via a first pin, and the proximal end of the first brick segment is connected to the distal end of the third brick segment at the second joint via a second pin.

2. The lead of claim 1, wherein the electrode comprises one or more support cables, wherein a first support cable of the one or more support cables extends along the first, second, and third brick segments and across the first and second joints and is affixed to each of the first, second, and third brick segments to secure the brick segments to one another in the line.

3. The lead of claim 2, further comprising a lead body extending from the electrode to the pulse generator, the lead body including at least one electrical wire electrically connected to the pulse generator and the electrode to convey electrical energy from the pulse generator to the electrode for delivering the high-voltage shocks.

4. The lead of claim 2, wherein the one or more support cables are electrically conductive and provide an electrically conductive pathway between the brick segments.

5. The lead of claim 2, wherein each of the brick segments defines a hollow cavity through a respective body of the brick segment, and the hollow cavities of the brick segments align to form a central channel of the electrode, wherein the one or more support cables are disposed within the central channel and affix to interior surfaces of the bodies of the brick segments.

6. The lead of claim 2, wherein each of the brick segments has a body that has an oblong shape with first and second lateral portions, the body defining one of grooves or apertures through a length of the body at the first and second lateral portions configured to receive the one or more support cables therein.

7. The lead of claim 1, wherein the distal end of the first brick segment nests within the proximal end of the second brick segment at the first joint.

8. The lead of claim 7, wherein the first brick segment is pivotable relative to the second brick segment at the first joint.

9. The lead of claim 1, wherein the brick segments include a first end piece at a proximal end of the electrode, a second end piece at a distal end of the electrode, and a plurality of middle pieces between the first and second end pieces in the line, wherein the middle pieces have a same size and shape as one another.

10. The lead of claim 1, wherein each of the brick segments has an oblong cross-sectional shape.

11. The lead of claim 1, wherein the electrode is a first electrode and the lead includes a second electrode configured to provide second high-voltage shocks for the defibrillation therapy, the second electrode disposed, along a length of the lead, between the first electrode and a proximal end of the lead, the proximal end configured to connect to the pulse generator of the IMD.

12. A method of producing a lead for an implantable medical device (IMD), the method comprising:

forming an electrode by mechanically connecting a plurality of brick segments to one another in a line, wherein the brick segments are discrete, electrically conductive, and electrically connected to one another, wherein a distal end of a first brick segment of the electrode is connected to a proximal end of a second brick segment of the electrode at a first joint, and a proximal end of the first brick segment is connected to a distal end of a third brick segment of the electrode at a second joint, the brick segments configured to be powered by a pulse generator of the IMD to deliver high-voltage shocks for defibrillation therapy, wherein the distal end of the first brick segment nests within the proximal end of the second brick segment at the first joint, and wherein the first brick segment is pivotable relative to the second brick segment at the first joint.

13. The method of claim 12, wherein forming the electrode comprises affixing one or more support cables, that extend along the brick segments, to the brick segments to secure the brick segments one another in the line, wherein the one or more support cables are affixed by extending a first support cable of the one or more support cables along the first, second, and third brick segments and across the first and second joints, and securing the first support cable to each of the first, second, and third brick segments.

14. The method of claim 13, further comprising securing a lead body to the electrode and electrically connecting the lead body to the electrode, the lead body including at least one electrical wire electrically connected to the pulse generator and configured to convey power from the pulse generator to the electrode for the defibrillation therapy.

15. The method of claim 13, further comprising welding the one or more support cables to the brick segments.

16. The method of claim 13, further comprising crimping the brick segments onto the one or more support cables to affix the one or more support cables to the brick segments.

17. The method of claim 12, wherein forming the electrode comprises nesting the distal end of the first brick segment within the proximal end of the second brick segment at the first joint.

18. The method of claim 12, wherein each of the brick segments has an oblong cross-sectional shape.

19. The method of claim 12, further comprising implanting the lead such that the electrode is disposed in a subcutaneous location within a patient.

20. An implantable medical device (IMD) comprising:

a pulse generator; and a lead comprising a lead body and an electrode, the lead body mechanically and electrically connected to both the pulse generator and the electrode, and extending from the pulse generator to the electrode, the electrode comprising a plurality of brick segments that are discrete and mechanically connected to one another in a line, wherein the brick segments are electrically conductive and electrically connected to one another, wherein a distal end of a first brick segment of the electrode is connected to a proximal end of a second brick segment of the electrode at a first joint, and the distal end of the first brick segment is nested within the proximal end of the second brick segment, wherein the distal end of the first brick segment nests within the proximal end of the second brick segment at the first joint;

wherein the first brick segment is pivotable relative to the second brick segment at the first joint;

wherein the pulse generator is configured to power the brick segments of the electrode, via the lead body, to deliver high-voltage shocks for defibrillation therapy.

* * * * *